United States Patent
King et al.

(10) Patent No.: US 11,638,564 B2
(45) Date of Patent: May 2, 2023

(54) MEDICAL MONITORING SYSTEM

(71) Applicant: BioLink Systems, LLC, Covington, KY (US)

(72) Inventors: Roger King, Hamilton, OH (US); Ken Heyl, Birmingham, AL (US); Tim King, Batavia, OH (US); Alex Matsukevich, Batavia, OH (US); Tim Gardner, Batavia, OH (US)

(73) Assignee: BioLink Systems, LLC, Covington, KY (US)

( * ) Notice: Subject to any disclaimer, the term of this patent is extended or adjusted under 35 U.S.C. 154(b) by 0 days.

(21) Appl. No.: 17/411,006

(22) Filed: Aug. 24, 2021

(65) Prior Publication Data

US 2023/0068111 A1  Mar. 2, 2023
US 2023/0068111 A1  Mar. 2, 2023

(51) Int. Cl.
*A61B 5/00* (2006.01)

(52) U.S. Cl.
CPC ............ *A61B 5/747* (2013.01); *A61B 5/0022* (2013.01); *A61B 5/6823* (2013.01); *A61B 5/6824* (2013.01); *A61B 5/7264* (2013.01); *A61B 5/746* (2013.01); *A61B 5/7475* (2013.01); *A61B 2505/07* (2013.01)

(58) Field of Classification Search
CPC ..... A61B 5/0022; A61B 5/747; A61B 5/6823; A61B 5/6824; A61B 5/7264; A61B 5/7475; A61B 2505/07; A61B 5/746; G16H 10/60; G16H 50/00; G16H 50/20; G16H 50/30
See application file for complete search history.

(56) References Cited

U.S. PATENT DOCUMENTS

| | | | |
|---|---|---|---|
| 5,557,263 A  | 9/1996  | Fisher et al. |
| 7,053,781 B1 | 5/2006  | Haire et al. |
| 7,559,902 B2 | 7/2009  | Ting et al. |
| 7,977,529 B2 | 7/2011  | Bergman et al. |
| 7,996,148 B2 | 8/2011  | Bergman et al. |
| 8,145,422 B2 | 3/2012  | Bergman et al. |
| 8,788,195 B2 | 7/2014  | Bergman et al. |
| 9,107,776 B2 | 8/2015  | Bergman et al. |
| 9,224,102 B2 | 12/2015 | Bergman et al. |

(Continued)

FOREIGN PATENT DOCUMENTS

| | | |
|---|---|---|
| JP | 2017189348 | 10/2017 |
| WO | 2005015477 | 2/2005 |
| WO | 2008026123 | 3/2008 |

OTHER PUBLICATIONS

PCT-US2019-060421 International Search Report and Written Opinion, dated Mar. 12, 2020.

(Continued)

*Primary Examiner* — John R Downey
(74) *Attorney, Agent, or Firm* — Chris Tanner; FYPA PLLC

(57) ABSTRACT

A medical monitoring system for use in residential facilities, nursing homes, or home environments is disclosed. The system utilizes a variety of modules and wearable medical devices that convey vital patient information to a series of smart hubs which are connected to the cloud. In the event a change in medical status of a patient occurs, the health care workers receive an Alert notifying them of which specific patient needs attention. The system is monitored using a specialized dashboard.

19 Claims, 23 Drawing Sheets

(56) References Cited

U.S. PATENT DOCUMENTS

| | | |
|---|---|---|
| 9,283,123 B2 | 3/2016 | Bergman et al. |
| 9,314,381 B2 | 4/2016 | Bergman et al. |
| 9,646,073 B2 | 5/2017 | Bergman et al. |
| 9,665,639 B2 | 5/2017 | Bergman et al. |
| 9,713,554 B2 | 7/2017 | Bergman et al. |
| 9,913,608 B2 | 3/2018 | Bergman et al. |
| 10,322,036 B2 | 6/2019 | Haire et al. |
| 10,404,704 B2 * | 9/2019 | Phillips ............... H04L 63/10 |
| 10,561,541 B1 | 2/2020 | Heyl et al. |
| 10,600,204 B1 * | 3/2020 | Rush ................... A61B 5/746 |
| 10,713,372 B1 | 7/2020 | Heyl et al. |
| 10,786,210 B1 | 9/2020 | Heyl et al. |
| 10,821,034 B2 | 11/2020 | Heyl et al. |
| 10,940,484 B2 | 3/2021 | Heyl et al. |
| 11,020,285 B1 | 6/2021 | King et al. |
| 2002/0128868 A1 * | 9/2002 | Lonski ................. G16H 15/00 |
| | | 705/2 |
| 2004/0142686 A1 * | 7/2004 | Kirkup ............... H04W 12/128 |
| | | 455/418 |
| 2005/0060198 A1 * | 3/2005 | Bayne .................. G16H 10/60 |
| | | 705/2 |
| 2008/0242945 A1 * | 10/2008 | Gugliotti ............. A61B 5/0022 |
| | | 600/300 |
| 2010/0198614 A1 * | 8/2010 | Chopra ................ G16H 10/60 |
| | | 705/2 |
| 2011/0001605 A1 | 1/2011 | Kiani |
| 2012/0296235 A1 * | 11/2012 | Rupp .................... A61B 5/1128 |
| | | 600/595 |
| 2013/0024029 A1 * | 1/2013 | Tran .................... A61B 5/0205 |
| | | 700/278 |
| 2013/0054467 A1 | 2/2013 | Dala et al. |
| 2013/0124227 A1 * | 5/2013 | Ellis .................... G16H 40/20 |
| | | 705/3 |
| 2013/0282438 A1 | 10/2013 | Hunter |
| 2013/0325503 A1 * | 12/2013 | Abrahams ............ G16H 15/00 |
| | | 705/2 |
| 2014/0018638 A1 * | 1/2014 | Chatterjee ........... A61B 5/4884 |
| | | 600/301 |
| 2014/0288996 A1 * | 9/2014 | Rence ................ G06Q 10/0635 |
| | | 705/7.28 |
| 2015/0213205 A1 * | 7/2015 | Van De Sluis ........ G16H 40/20 |
| | | 705/2 |
| 2015/0257942 A1 | 9/2015 | Kim |
| 2015/0302539 A1 * | 10/2015 | Mazar .................... G08B 21/02 |
| | | 705/3 |
| 2016/0070863 A1 * | 3/2016 | Harber .................. G16H 10/60 |
| | | 705/3 |
| 2016/0095758 A1 | 4/2016 | Haire et al. |
| 2017/0134937 A1 * | 5/2017 | Miller ............... G06Q 20/3829 |
| 2017/0287316 A1 * | 10/2017 | Wildman ............... G08B 25/10 |
| 2017/0308665 A1 * | 10/2017 | Heck ................... A61M 5/14244 |
| 2018/0000385 A1 * | 1/2018 | Heaton .............. G08B 21/0446 |
| 2018/0019878 A1 * | 1/2018 | Jiang .................... H04L 9/0894 |
| 2019/0108908 A1 * | 4/2019 | Faulks ................ G08B 27/005 |
| 2019/0209022 A1 * | 7/2019 | Sobol .................. A61B 5/0022 |
| 2019/0239775 A1 * | 8/2019 | Movva ................. G16H 40/67 |
| 2019/0307405 A1 * | 10/2019 | Terry .................... G16H 40/20 |
| 2019/0313913 A1 * | 10/2019 | Fu ........................ A61B 5/0022 |
| 2019/0336085 A1 * | 11/2019 | Kayser ................. A61B 5/447 |
| 2020/0287726 A1 * | 9/2020 | Garnier ................ H04L 67/125 |
| 2020/0365264 A1 * | 11/2020 | Girardeau ............. G06F 3/0482 |
| 2021/0183504 A1 * | 6/2021 | Agdeppa ............... A61B 5/08 |
| 2021/0196406 A1 * | 7/2021 | Mahadik ............... G16H 40/63 |
| 2021/0219873 A1 * | 7/2021 | Receveur ............. G16H 40/63 |
| 2022/0139569 A1 * | 5/2022 | Gilbert ................. G16H 40/63 |
| | | 705/2 |

OTHER PUBLICATIONS

PCT-US2020-034439 International Search Report and Written Opinion, dated Sep. 10, 2020.

PCT-US2019-060421 International Preliminary Report on Patentability, dated Mar. 19, 2021.

* cited by examiner

FIG. 4 (Assignment process)

Manorcare Assisted Living

Tim Gardner•ADMIN ⇨ Logout

GENERAL
- Alerts
- Patients

ADMINISTRATOR
- Staff Management
- Device Management

Facility Alerts

| By Alert | By Patient | All Alerts ⑧ | Priority Escalated ⓪ | Escalated ⓪ | Other ⑧ |
|---|---|---|---|---|---|

Other

Finney, Albert
Hygiene
⏱10:31 AM 🗓 Apr 15, 2021 🔗 MOD-222-AF

Finney, Albert
Position
⏱11:50 AM 🗓 Apr 15, 2021 🔗 MOD-222-AF

Affleck, Ben
Module Disconnected
⏱12:59 PM 🗓 Apr 15, 2021 🔗 WBL-333-BA

Brown, Bobby
Urinary Output
⏱01:44 PM 🗓 Apr 15, 2021 🔗 MOD-222-BB

Downer, Debbie
Prohibited Position Back
⏱02:01 PM 🗓 Apr 15, 2021 🔗 MOD-222-BB

Medical Monitoring system 100

FIG. 6

Manorcare Assisted Living of Vermont    Tim Gardner•ADMIN (→ Logout)

GENERAL
- Alerts
- Patients

ADMINISTRATOR
- Staff Management
- Device Management

Facility Alerts

| By Alert | By Patient | All Alerts ⑧ | Priority Escalated ⓪ | Escalated ⓪ | Other ⑧ |

Other

| | | |
|---|---|---|
| Finney, Albert Hygiene @10:31 AM @ Apr 15, 2021 @ MOD-222-AF | 🔔 ⋯ | Finney, Albert — example bell icon 704 |
| Finney, Albert Position @11:50 AM @ Apr 15, 2021 @ MOD-222-AF | 🔔 ⋯ | Hygiene — Patient has been changed too quickly from an incontinence episode @ MOD-222-AF ⋯  Alert Status: OPEN |
| Affleck, Ben Module Disconnected @12:59 PM @ Apr 15, 2021 @ WBL-333-BA | 🔔 ⋯ | Alert#  Severity Value  Threshold Breached  Date  Time |
| Brown, Bobby Urinary Output @01:44 PM @ Apr 15, 2021 @ MOD-222-BB | 🔔 ⋯ | 1st alert [OTHER]  1?  Above Undefined?  Apr 15,2021  10:31 AM |
| Downer, Debbie Prohibited Position Back @02:01 PM @ Apr 15, 2021 @ MOD-222-BB | 🔔 ⋯ | ≡ CHANGE PATIENT THRESHOLDS |

Patient Alert History                                     Date Range: Last 30 Days ▼

| Details | Alert | Device ID | Device Type | Date | Time Respond |
|---|---|---|---|---|---|
| DETAILS | Hygiene | *2-AF | Module | April 15, 2021 | 10:31 AM |
| DETAILS | Position | *2-AF | Module | April 15, 2021 | 11:50 AM |

Medical Monitoring system 100

FIG. 7

Manorcare Assisted Living   Tim Gardner•ADMIN ⊖ Logout

GENERAL
- Alerts
- Patients

ADMINISTRATOR
- Staff Management
- Device Management

Facility Alerts

| By Alert | By Patient | All Alerts (8) | Priority Escalated (0) | Escalated (0) | Other (8) |

No Active Alerts

Finney, Albert                                                                                  MOD-222-AF ...

Hygiene
Patient has been changed too quickly
from an incontinence episode

| Alert# | Severity | Value | Threshold | | Date | Time |
|---|---|---|---|---|---|---|
| 1st alert | OTHER | 1? | Above Undefined? | Breached | Apr 15, 2021 | 10:31 AM |

≡ CHANGE PATIENT THRESHOLDS

Alert Status: OPEN

Patient Alert History                                              Date Range
                                                                   Last 30 Days ▼

| Details | Alert | Device ID | Device Type | Date | Time Respond |
|---|---|---|---|---|---|
| DETAILS | Hygiene | *2-AF | Module | April 15, 2021 | 10:31 AM |
| DETAILS | Position | *2-AF | Module | April 15, 2021 | 11:50 AM |

Medical Monitoring system 100

FIG. 8

Manorcare Assisted Living of Vermont

Tim Gardner•ADMIN ⊙ Logout

Facility Alerts

| By Alert | By Patient | All Alerts ⑧ | Priority Escalated ⓪ | Escalated ⓪ | Other ⑧ |

Affleck, Ben

Module Disconnected
Brief not connected to the module correctly
⊙12:59 PM ⊟ Apr 15, 2021 ⓘ WBL-333-BA Brown, Bobby Urinary Output
Patient has gone too long without an incontinence episode
⊙01:44 PM ⊟ Apr 15, 2021 ⓘ MOD-222-BB Chaplin, Charlie Incontinence Episode
Incontinence episode detected by brief module
⊙08:05 AM ⊟ Apr 15, 2021 ⓘ MOD-222-CC Downer, Debbie Prohibited Position Back
Patient needs moved–cannot lay on back
⊙10:31 AM ⊟ Apr 15, 2021 ⓘ MOD-222-DD Finney, Albert Hygiene                                                      ⓘ MOD-222-AF •••
Patient has been changed too quickly
from an incontinence episode Alert#   Severity   Value   Threshold       Alert Status: OPEN
                            Breached        Date        Time 1st alert [OTHER]    1?     Above           Apr 15, 2021  10:31 AM
                            Undefined?

≡ CHANGE PATIENT THRESHOLDS

Patient Alert History                        Date Range
                                             Last 30 Days ▼

Details   Alert      Device    Device
                     ID        Type          Date          Time   Respond

[DETAILS] Hygiene    *2-AF     Module        April 15, 2021 10:31 AM
[DETAILS] Position   *2-AF     Module        April 15, 2021 11:50 AM

FIG. 9

Manorcare Assisted Living of Vermont | Tim Gardner•ADMIN ⊖ Logout

GENERAL
- Alerts
- Patients

ADMINISTRATOR
- Staff Management
- Device Management

Facility Alerts

Downer, Debbie

Prohibited Position Back
Patient needs moved-cannot lay on back
⊙ 10:31 AM ⊟ Apr 15, 2021 ⊕ MOD-222-DD Prohibited Position Prone
Patient needs moved-cannot lay prone (on stomach)
⊙ 10:31 AM ⊟ Apr 15, 2021 ⊕ MOD-222-DD Incontinence Episode
Incontinence episode detected by brief module
⊙ 08:05 AM ⊟ Apr 15, 2021 ⊕ MOD-222-CC

Finney, Albert

Hygiene
Patient has been changed too quickly from an incontinence episode
⊙ 12:05 AM ⊟ Apr 15, 2021 ⊕ MOD-222-CC Position
Patient needs moved-in same position too long
⊙ 11:05 AM ⊟ Apr 15, 2021 ⊕ MOD-222-AF

Finney, Albert                                      ⊕ MOD-222-AF ···

Position
Patient needs moved-in same position too long           Alert Status: OPEN

| Alert# | Severity | Value | Threshold Breached | Date | Time |
|---|---|---|---|---|---|
| 1st alert | OTHER | 1? | Above Undefined? | Apr 15, 2021 | 11:05 AM |

≡ CHANGE PATIENT THRESHOLDS

Patient Alert History                                   Date Range: Last 30 Days ▼

| Details | Alert | Device ID | Device Type | Date | Time | Respond |
|---|---|---|---|---|---|---|
| DETAILS | Hygiene | *2-AF | Module | April 15, 2021 | 10:31 AM | |
| DETAILS | Position | *2-AF | Module | April 15, 2021 | 11:50 AM | |

1-2 of 2   <  >

Medical Monitoring system 100

FIG. 12

Manorcare Assisted Living    Tim Gardner•ADMIN (→ Logout)

GENERAL
- Alerts
- Patients

ADMINISTRATOR
- Staff Management
- Device Management

Facility Alerts

| Affleck, Ben | Affleck, Ben | ⊕ MOD-333-BA... |
|---|---|---|

Module Disconnected   Module Disconnected   Alert Status: OPEN
Brief not connected to the module correctly   Brief not connected to the module correctly
⊙12:59 PM ▫ Apr 15, 2021 ⊕ WBL-333-BA

| Alert# | Severity | Value | Threshold Breached | Date | Time |
|---|---|---|---|---|---|
| 1st alert | OTHER | 1? | Above Undefined? | Apr 15, 2021 | 12:59 PM |

≡ CHANGE PATIENT THRESHOLDS

Brown, Bobby
Urinary Output
Patient has gone too long without an incontinence episode
⊙01:44 PM ▫ Apr 15, 2021 ⊕ MOD-222-BB Patient Alert History    Date Range: Last 30 Days ▾

| Device ID | Device Type | Date | Time | Responder | Result |
|---|---|---|---|---|---|
| *3-BA Wearable | April 15, 2021 | 08:05 AM | Stephen, Joseph | Inaccurate alert |
| *3-BA Wearable | April 15, 2021 | 12:59 PM | | |

Chaplin, Charlie
Incontinence Episode
Incontinence episode detected by brief module
⊙08:05 AM ▫ Apr 15, 2021 ⊕ MOD-222-CC

Downer, Debbie
Prohibited Position Back
Patient needs moved-cannot lay on back
⊙10:31 AM ▫ Apr 15, 2021 ⊕ MOD-222-DD 1 row selected    1-2 of 2 ‹ ›

Medical Monitoring system 100

FIG. 13

Manorcare Assisted Living     Tim Gardner•ADMIN ⊙ Logout

GENERAL
- Alerts
- Patients

ADMINISTRATOR
- Staff Management
- Device Management

Facility Alerts

| | | |
|---|---|---|
| Affleck, Ben | Affleck, Ben | ⊙ MOD-333-BA ... |
| Module Disconnected | Module Disconnected | Alert Status: CLOSED |
| Brief not connected to the module correctly | Brief not connected to the module correctly | |
| ⊙12:59 PM ⊟ Apr 15, 2021 ⊙ WBL-333-BA | | |
| Brown, Bobby | Alert#   Severity   Value   Threshold Breached   Date   Time | |
| Urinary Output | 1st alert   OTHER   1?   Above Undefined?   Apr 15,2021   12:59 PM | |
| Patient has gone too long without an incontinence episode | ≡ CHANGE PATIENT THRESHOLDS | |
| ⊙01:44 PM ⊟ Apr 15, 2021 ⊙ MOD-222-BB | | |
| Chaplin, Charlie | Patient Alert History | Date Range: Last 30 Days ▼ |
| Incontinence Episode | | |
| Incontinence episode detected by brief module | Details   Alert   Device ID   Device Type   Date   Time   Resp | |
| ⊙08:05 AM ⊟ Apr 15, 2021 ⊙ MOD-222-CC | DETAILS   Hygiene   *3-BA   Wearable   April 15,2021   10:31 AM | |
| Downer, Debbie | DETAILS   Position   *3-BA   Wearable   April 15,2021   11:50 AM | |
| Prohibited Position Back | | |
| Patient needs moved–cannot lay on back | 1-2 of 2   <   > | |
| ⊙10:31 AM ⊟ Apr 15, 2021 ⊙ MOD-222-DD | | |

1 row selected

Medical Monitoring system 100

FIG. 14

Manorcare Assisted Living of Vermont

GENERAL
- Alerts
- Patients

ADMINISTRATOR
- Staff Management
- Device Management

| Facility Alerts | | | | Facility Alerts |
|---|---|---|---|---|
| Affleck, Ben | | | Affleck, Ben | All Alerts (8) Priority (0) Escalated(0) Other(8) Escalated |
| Module Disconnected Brief not connected to the module correctly | | | Module Dis Brief not co | Other |
| 12:59 PM · Apr 15, 2021 · WBL-333-BA | | | | Finney, Albert Hygiene |
| Brown, Bobby | | | Alert# Se | 10:31 AM · Apr 15, 2021 · MOD-222-AF |
| Urinary Output Patient has gone too long without an incontinence episode | | | 1st alert OT | Finney, Albert Position |
| 01:44 PM · Apr 15, 2021 · MOD-222-BB | | | ≡ CHANGE | 11:50 AM · Apr 15, 2021 · MOD-222-AF |
| Chaplin, Charlie | | | Patient Alert | Affleck, Ben Module Disconnected |
| Incontinence Episode Incontinence episode detected by brief module | | | Details | 12:59 PM · Apr 15, 2021 · WBL-333-BA |
| 08:05 AM · Apr 15, 2021 · MOD-222-CC | | | | Brown, Bobby Urinary Output |
| Downer, Debbie | | | DETAILS | 01:44 PM · Apr 15, 2021 · MOD-222-BB |
| Prohibited Position Back Patient needs moved-cannot lay on back | | | DETAILS | Downer, Debbie Prohibited Position Back |
| 10:31 AM · Apr 15, 2021 · MOD-222-DD | | | | 02:01 PM · Apr 15, 2021 · MOD-222-BB |
| | | | 1 row selected | Downer, Debbie Prohibited Position Prone |
| | | | | 03:25 PM · Apr 15, 2021 · MOD-222-DD |

Manorcare Assisted Living  Tim Gardner•ADMIN ⇨ Logout

GENERAL  Facility Alerts

🔔 Alerts  | By Alert | By Patient | All Alerts ⑧ | Priority Escalated ⓪ | Escalated ⓪ | Other ⑧ |

👤 Patients

Priority Escalated

ADMINISTRATOR   Capp, ANdy
👥 Staff Management    🔔 Abnormal Heart rate          Afflec, Ben       ⚭ Wearable WBL-333-BA ···
🔌 Device Management   ⓧ 01:59 AM ⊟ Apr 15, 2021 ⚭ WBL-333-AC
                                        Module Disconnected
Escalated                              Brief not connected to the module
Falls, Betty                            correctly
   🔔 Abnormal Heart rate          Alert#   Severity   Value   Threshold   Alert Status: OPEN
   ⓧ 09:00 AM ⊟ Apr 15, 2021 ⚭ WBL-333-BF                    Breached
Other                                  1st    OTHER    0n/a   Above      Date         Time
Finney, Albert                         alert                  Undefined  Apr 15, 2021  08:05 AM
   🔔 Position                                                n/a
   ⓧ 06:00 AM ⊟ Apr 15, 2021 ⚭ MOD-222-AF
Davis, Edna                            ≡ CHANGE PATIENT THRESHOLDS
   🔔 Inconsistence Episode
   ⓧ 08:05 AM ⊟ Apr 15, 2021 ⚭ MOD-222-ED    Patient Alert History              Date Range
                                                                                 Last 30 Days ▼
Afflec, Ben                           Device
   Module Disconnected ←currently selected  Type [i]  Date          Time     Responder   Result
                                      Wearable  April 15,2021  10:31 AM                 Open
                                      ↑
                                      selection indicator
                                      (mouse hover)

Wearable  Apr 15,2021   08:05 AM                  Open

↖ Medical
  Monitoring
  system 100

FIG. 18

Manorcare Assisted Living                                    Tim Gardner•ADMIN ⟲ Logout

GENERAL
⚠ Alerts
👤 Patients

ADMINISTRATOR
☎ Staff Management
🖥 Device Management

Facility Alerts

| By Alert | By Patient | All Alerts ⑧ | Priority Escalated ⓪ | Escalated ⓪ | Other ⑧ |

Priority Escalated

Finney, Albert

Finney, Albert ⚠···    Position          ⓘ Wearable WBL-333-BA ···

Hygiene ⚠···    Patient need moved-in same position too long

⌚ 06:00 AM ⊟ Apr 15, 2021 ⓘ MOD-222-AF       Alert#   Severity   Value   Threshold Breached   Date   Time   Alert Status: OPEN Finney, Albert ⚠···

Position         1st alert   OTHER   1 degrees   Above Undefined degrees   Apr 15, 2021   11:50 AM ⌚ 08:05 AM ⊟ Apr 15, 2021 ⓘ MOD-222-ED Affec, Ben ⚠···     ≡CHANGE PATIENT THRESHOLDS 🖱 ←— selection indicator (mouse hover)

Module Disconnected    Patient Alert History

| 12:59 PM ⊟ Apr 15, 2021 ⓘ WBL-333-BA |    Details   Alert   Device ID   Device Type   Date   Time   Resp Brown, Bobby ⚠···

Urinary Output

01:44 PM ⊟ Apr 15, 2021 ⓘ MOD-222-BB    DETAILS Hygiene *2-AF Module April 15, 2021 10:31 AM Downer, Debbie ⚠···

Prohibited Position Back

02:01 PM ⊟ Apr 15, 2021 ⓘ MOD-222-DD    DETAILS Position *2-AF Module April 15, 2021 11:50 AM Date Range — Last 30 Days ▼

⤺ example columns of patient data

↖ Medical Monitoring system 100

Manorcare Assisted Living  Tim Gardner•ADMIN ↪Logout

GENERAL
- Alerts

ADMINISTRATOR
- Staff Management
- Device Management

Facility Patients    ☐ ADD NEW PATIENT

| | |
|---|---|
| Affleck, Ben | ACTIVE |
| Chaplin, Charlie | ACTIVE |
| Clark, Dick | ACTIVE |
| Downer, Debbie | ACTIVE |
| Falls, Betty | ACTIVE |
| Finney, Albert | ACTIVE |
| Patient, Demo | ACTIVE |
| Brown, Bobby | INACTIVE |
| Capp, Andy | INACTIVE |
| Davis, Edna | INACTIVE |

Patient Alert Rules

| Device type | Alert Rule Name | Modified By | Facility Default Min | Max | Unit | Patient Override Min | Max | |
|---|---|---|---|---|---|---|---|---|
| Wear-able | Abnormal heart rate Rate too low or too high | McCoy, Leonard | 50 | 150 | BPM | 60 | 130 | RESET |
| Module | Incontinence Episode Range in which device will alert for incontinence episode triggers | Pierce, Hawkeye | 50 | 150 | ounces | 60 | 130 | RESET |
| Module | Pulse Oximeter Frequency in seconds (1-90 seconds max) | Houser, Doogie | 50 | 150 | SpO2 | 60 | 130 | RESET |

Medical Monitoring system 100

MEDICAL MONITORING SYSTEM

BACKGROUND OF THE INVENTION

Residential facilities, nursing homes, and home care environments all struggle with the same problem: having reliable accurate data regarding a patient's medical condition when the caregiver is not in the same room as the patient. Caring for patients is easier when caregivers can be notified of changes in medical conditions. Consequently, a system for obtaining reliable accurate assessment of the health of a group of patients is advantageous.

BRIEF DESCRIPTION OF THE DRAWINGS

FIG. 6 shows selection of a specific types of alerts;

FIG. 7 shows details about a particular Alert;

FIG. 8 shows Alerts sorted by escalation level;

FIG. 9 shows an example "priority escalated" Alert;

FIG. 12 shows example of a positional Alert;

FIG. 13 shows an example Alert about to be closed for being inaccurate;

FIG. 14 shows the Alert from FIG. 13 as being closed;

FIG. 15 is a GUI showing a user-selection of details from a column of Alerts related to a specific patient;

FIG. 16 shows the GUI of FIG. 15 except with the column of Alerts removed;

FIG. 17 shows example of multiple heart rate Alerts;

FIG. 18 shows an example GUI button which takes users to a particular patient in the patient view;

FIG. 19 shows an example of column of patient data;

FIG. 20 shows example GUI showing the amount of devices associated with a particular patient;

FIG. 21 shows an example listing for a new patient check-in;

FIG. 22 shows an example GUI for configuring what constitutes an abnormal heart rate Alert for a specific patient; and FIG. 23 show an example GUI of a patient discharge.

PREFACE/SEMANTICS

The smart hub shown in various of the drawings herein (e.g. FIG. 1) is shown as a type of (literal) "raspberry", but that is for convenience only, and quick ease of recognition, in that some embodiments of the smart hub are raspberry pi's. The smart hub may come in many forms that are not a raspberry pi, one of which is Arduino. Other customized and proprietary hardware could also be implemented for the smart hub.

Next, within this disclosure, the expression Alert will be spelled in Mixed Case because this is a specialized term having a specific meaning within this disclosure that may be different than its common, generally accepted meaning. This will also hold true for the expressions Assignment, and Registration, which in this disclosure will be considered Terms of Art and used somewhat outside their conventional meaning.

Another semantic is the word "dashboard", as the embodiments herein recite both a system dashboard 500 and a facility dashboard 800. These are not the same and have different purposes and different users, but the expression "dashboard" is particularly applicable and salient for implementations have a GUI front-end. This disclosure will never refer to just a dashboard, but instead will always recite system dashboard 500 or facility dashboard 800.

Finally, this disclosure will discuss both an institutional embodiment used by e.g. residential facilities or nursing homes, as well as a home embodiment that is used by a caretaker (e.g. family member) responsible for potentially just one person or at most two persons. For convenient reference, both will be referred to as "system 100", but there are some differences although many more commonalities.

Overview\Topology

Figure 1:
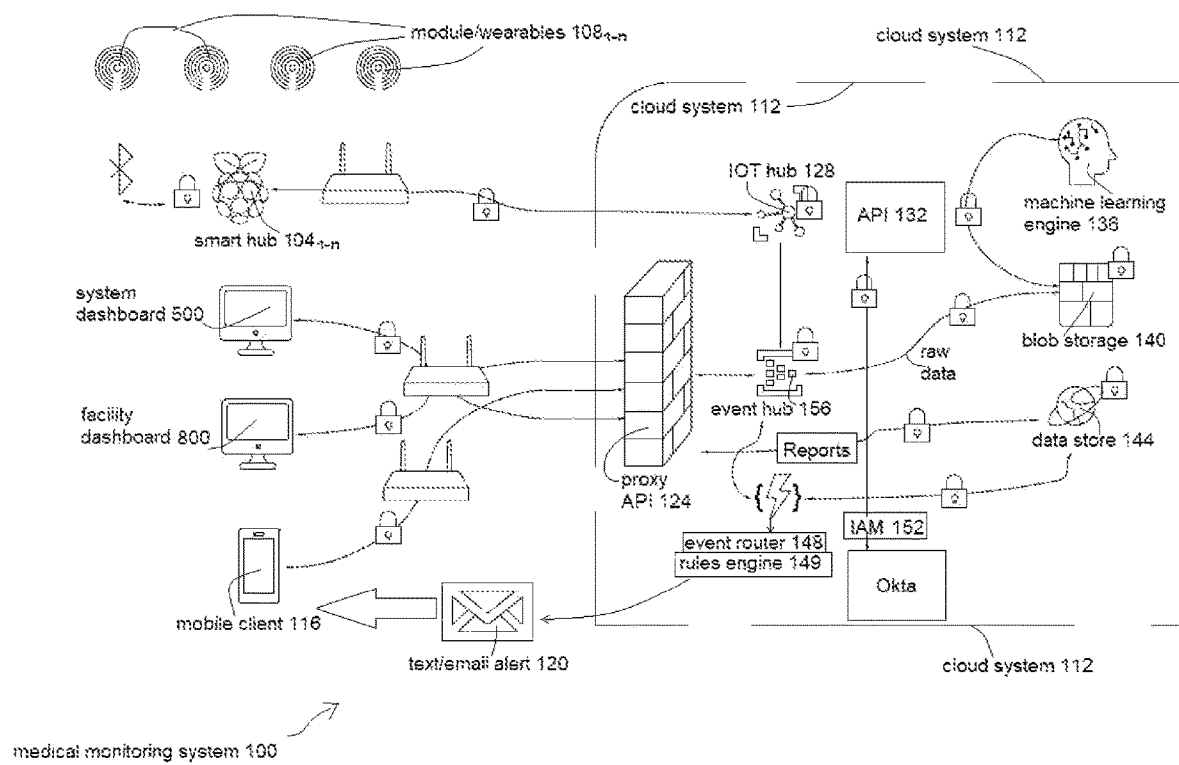
FIG. 1 shows an example embodiment of a medical monitoring system.

FIG. 1 (topology) shows an example embodiment of a medical monitoring system 100 comprising one or more patient modules/wearables $108_{1-n}$ that communicate with a cloud system 112 through a series of smart hubs $104_{1-n}$. In an embodiment, the cloud system 112 could be implemented using Azure, or some other cloud mechanism. The modules/wearables 108 are described elsewhere in more detail, e.g. various U.S. Patents including but not limited to U.S. Pat. No. 10,940,484, Issued Mar. 9, 2021; U.S. Pat. No. 10,561,541, Issued Feb. 18, 2020; and U.S. Pat. No. 11,020,285, Issued Jun. 1, 2021, the entire contents of which are hereby incorporated by reference into this disclosure.

Within this disclosure, it will suffice to note the modules/wearables 108 are attached to a human patient one way or another (either waist, wrist, both, toe, or earlobe or other location), and convey medical data wirelessly to various points within a residential facility or nursing home or home environment.

For clarity, this disclosure will first assume that the module\wearables 108 will be communicating via Bluetooth, including sending data via Bluetooth to the one or more smart hubs $104_{1-n}$. However, other communication protocols such as Zigbee may also be used, but for clarity at least at first, Bluetooth Low Energy (BTLE) will be assumed.

There are a variety of ways that the medical monitoring system 100 communicates with the Internet, so to eliminate confusion within this disclosure, one way will be assumed to be (at least partly) using a residential facility's local Wi-Fi. However, one or more of the smart hubs 104 may also have the ability to reach the Internet, and therefore the cloud system 112. Because the system 100 can be implemented in a residential facility, or in a home, it would take too long to diagram out each separate way Internet connectivity could be achieved, and would be a distraction from other more prominent portions of the embodiments herein.

Instead, it will be assumed that all of the smart hubs 104 communicate with the cloud system 112, either directly or perhaps through one "master" smart hub 104. Either way, as soon as a smart hub $104_1$, smart hub $104_2$, or smart hub $104_3$ receive data from a module\wearable 108, that smart hub will send it right away to the cloud system 112. In an embodiment, the cloud system 112 can comprise Azure mechanisms and Azure-related implementations. However, the cloud system 112 is not limited solely to Azure-related implementations.

In an embodiment the smart hubs 104 can be raspberry pi's, but may be Arduino or other processor. In any case, as stated these smart hubs 104 are spread around an entire residential facility being served by the medical monitoring system 100, but where communication is encrypted, as symbolized by the various padlock icons in FIG. 1. The smart hubs 104 themselves will not be capable of decrypting that information, will instead be acting just as a pass-thru, and will be just forwarding that information through the Internet connection (e.g. native Wi-Fi) to the cloud system 112, specifically the IOT hub 128. The IOT hub 128 and cloud system 112 serve to look up an encryption key, decrypt data therein, and put that raw data into the event hub 156, at which point the raw data will be stored for long-term use within the blob storage 140.

Continuing with FIG. 1, the event router 148 comprises a rules engine 149 suitable for processing the raw data from the blob storage 140. If the raw data comprises patient measurements, patient metrics or conditions, and those measurements are outside of specific thresholds, the rules engine 149 within the event router 184 will generate an Alert, and that Alert will go out to do the mobile client 116 having a specialized mobile application loaded therein, via e.g. push notification. The Alerts can be sent via a variety of protocols, including but not limited to text messages or as emails, and will generally be sent to the mobile client 116.

At the same time, those Alerts will also be stored in the data store 144, so they can be historically looked up on the system dashboard 500. The system dashboard 500 will allow facility staff to log in, to view patients, to modify patient information, to set up new patients e.g. FIG. 21, to set up staff, added their information, and specify disabled or enabled areas. The system dashboard 500 will also enable users to reset their account information as well on the mobile client 116 application.

Health care workers, caregivers e.g. nurses and nurse Aides will be able to respond to most Alerts using the mobile app running on the mobile client 116. When someone responds to or acknowledges an Alert, they will be filling out an Alert questionnaire about the accuracy of the alert, e.g. what's causing the alert, how accurate, facilitate a doctor to investigate this further. For simplicity, speed, and ease-of-training, an embodiment of the app running on the mobile client 116 will have pull-down menus and pre-entered choices only, to make responding easier and more effective. However, it is also possible to have an embodiment in which the app running on the mobile client 116 allows for text-entry as well, and potentially even photographic input.

Next, the system dashboard 500 can set the status of a particular mobile client 116. The mobile client 116 is a cellphone-like device that is typically assigned to a health-care worker, and can be in various stages of repair, recharge, not removed from the residential facility or if removed, removed by accident. IOW, the mobile client 116 can be in a lot of different states. The mobile client 116 is intentionally disabled from having any other conventional mobile apps such as Facebook or Instagram. Instead, the mobile client 116 will have one usage, professional-only, and will not have much street value and cannot be hacked. But it will be necessary to for any residential facility or nursing home using the system 100 to inventory (verb) and manage the mobile clients 116, as these are an important part of an effective and successful implementation of the medical monitoring system 100.

It's possible for a mobile client 116 to also have a status of "unassigned". That mean not currently assigned to any health care worker, just an "unassigned" mobile client 116. One example of this might be a new mobile client 116, just sitting in inventory, but currently not attached to any facility-worker yet. That mobile client 116 won't be triggering Alerts, and won't be taking any measurements. If Alerts came from such a mobile client 116, a user of the system dashboard 500 could induce that something has gone wrong with the tracking of the mobile clients 116, or with the processing of Alerts somewhere within the system 100.

The facility dashboard 800 has a separate purpose from the system dashboard 500, and will be discussed elsewhere in this disclosure. The proxy API 124 and API 132 serve to provide developers of products intended to work with the system 100 a reliable and safe mechanism for interfacing therewith. The IAM 152 and Okta will be discussed in more detail elsewhere herein, but are used for verifying workers and caregivers to the medical monitoring system 100, and also controlling which types of workers have access to which parts.

All information in any particular Alert questionnaire gets stored and sent back to the cloud system 112. That again goes into long-term storage, e.g. blob storage 140, which then allows the machine learning to "learn" the Alert data. That in turn provides a feedback mechanism where an Alert goes out, a human worker takes a look at that Alert and (using the mobile client 116 and the app loaded therein) provides feedback on the quality of the information causing that Alert. That information gets fed back to the machine learning engine 136, which will eventually make the various Alerts even more accurate to the point where eventually, there becomes less need to manually set thresholds for each patient.

The system 100 has sufficient intelligence to set up at least a provisional baseline for each patient individually through the machine learning engine 136, and build a normal range for all the measurements. Then, for that given patient, if there's a measurement that's outside of the normal, that that would mean that this requires an intervention from facility staff.

Moving on to the padlock symbols occurring many places within (at least) FIG. 1, these signify securing the overall communication between e.g. module\wearable 108 and the smart hub 104, as well as between smart hub 104 and the cloud system 112 via encryption. An initial point of data weakness is the communication from the modules\wearables 108 to the smart hubs 104. Accordingly, the embodiments herein have included a mechanism created to secure that communication using encryption keys.

One of the challenges is that neither the smart hub 104 nor the modules\wearables 108 have any display-screen to speak of, although some have lights and a bit of blinking and "battery-low" features. To address this, the embodiments herein use a standard process of verifying a passkey and encryption key to set up an encryption process. Initially a new module\wearable 108 is brought into a facility, and is Registered with the medical monitoring system 100.

Registration of Wearables

Within this disclosure, the word "Registered" will mean receiving encryption keys, encrypting the data that is going to be passing along to the smart hub 104, and will be always spelled in Mixed Case in order to connote a specialized meaning outside its ordinary usage.

To Register a new module\wearable 108, the module\wearable 108 is set (configured) into a special pairing mode, at least within the BTLE embodiments. Within the Zigbee embodiments, some equivalent of a special pairing mode is also likely, although the word "pairing" may change, as that word is more often associated with BTLE. Once the special pairing mode happens, the app running on the mobile client 116 will be used to set up a Bluetooth (BTLE) secure connection, where it will get the (passcode) generated by the module\wearable 108, as well as generate its own special encryption key. A comparison of special encryption key and passcode is then made. If they match, that establishes that secure communication of the Bluetooth between the wearable 108 and the app on the mobile client 116. If they don't match, something went wrong in the Registration process and the app will post an error-GUI.

Each time a module/wearable 108 is Registered, a new (special) encryption key is generated. This process can be achieved where the module/wearable 108 being either on or off the patient's body. Next, there is only one special encryption key that gets set up for any module/wearable 108 at a time. Each time a module/wearable gets re-Registered, the old special encryption key gets discarded and a new one gets created.

Figure 2:
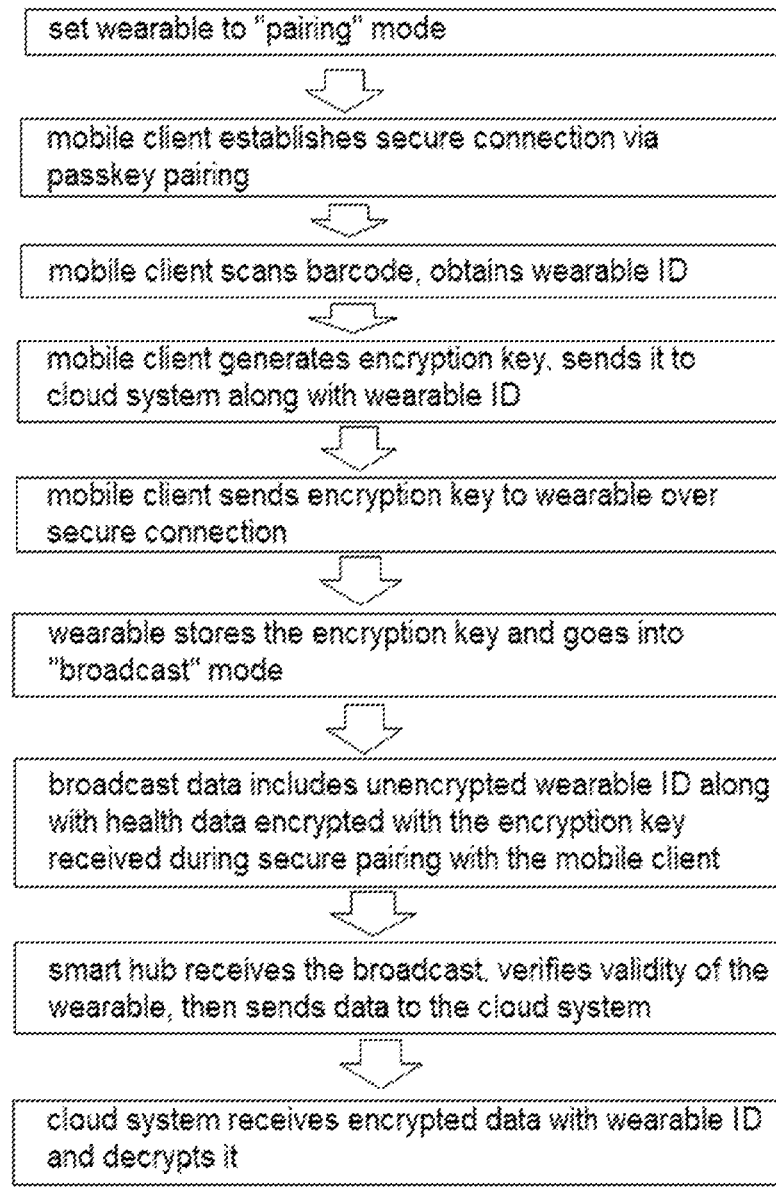
FIGS. 2 and 3 show example flowcharts of a Registration process.
Figure 3:
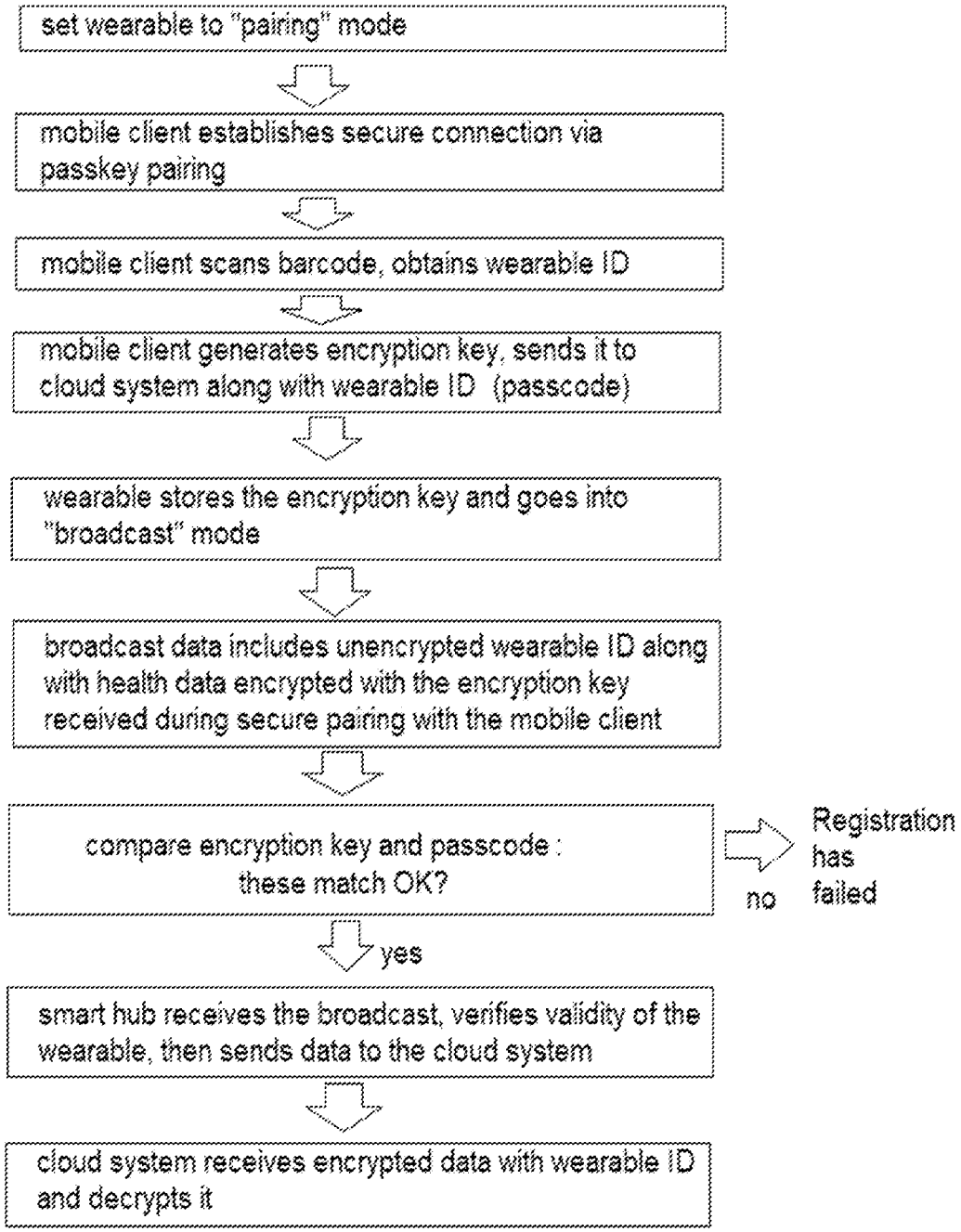

Most of the Registration process is shown in FIG. 2, but for brevity, the comparison of passkey and passcode is not shown therein. FIG. 3 shows another separate flowchart, overlapping with the flowchart of FIG. 2, but again simplified to fit on a single page. That is, FIGS. 2 and 3 show example non-limiting Registration flowcharts, but as summary-only. Other steps may occur that are not shown in FIGS. 2-3, and steps in FIGS. 2-3 may occasionally be omitted. The Registration process described herein may incorporate elements of both FIGS. 2 and 3, but may in some cases omit various portions. Thus, FIGS. 2 and 3 are for example purposes only, and should not be considered as limiting of the embodiments herein.

Once a proper match occurs, the app on the mobile client 116 will inquire to the cloud system 112 system to generate a normal encryption key. When it generates the normal encryption key, the cloud system 112 will assign that key to the ID of that module\wearable 108.

After that step is complete, the normal encryption key will get sent back to the mobile client 116, at which point the app running thereupon will send that normal encryption key to the module\wearable 108. Then, the module\wearable 108 will store that normal encryption key and go into the normal pairing mode and the normal broadcast mode. That means the smart hub 104 will turn over any Bluetooth communication that's encrypted.

It is not easy to have assurance of an effective encryption key comparison since there's no display screen on either device, either the smart hub 104 or the module\wearable 108. To counteract that problem, the data sent across this Bluetooth channel will be encrypted with the normal encryption key obtained in the previous step. Once this occurs, the smart hub 104 receives that data, where the only piece that will be un-encrypted in that data payload will be the ID of the module\wearable 108.

The smart hub 104 will then send the encrypted payload to the cloud system 112, along with the unencrypted wearable ID. Once the cloud system 112 receives that encrypted data, it will grab the wearable ID and look up the encryption key for that wearable ID. With that encryption key, it will decrypt that data and be able to process it and store it for further use.

In this way, the smart hub 104 has no knowledge of the actual information being sent, instead just passing it along to the cloud system 112. Similarly, all communications either to or from the smart hubs 104 are encrypted, such that hacking or invading or ransom-izing a smart hub 104 will yield zero useful information or data.

An important semantic issue needs to be conveyed here. The process of Registration means Register (verb) a module\wearable 108, not a patient. Meanwhile, the process of Assignment (noun) means take a Registered module\wearable 108, and Assign (verb) that wearable to a patient. Thus, the Registration of a module\wearable 108 will likely occur at a different time, and possibly by a different person, than an Assignment of that module\wearable 108 to a specific patient.

This ends the Registration section.

Assignment of Wearable

Figure 4:
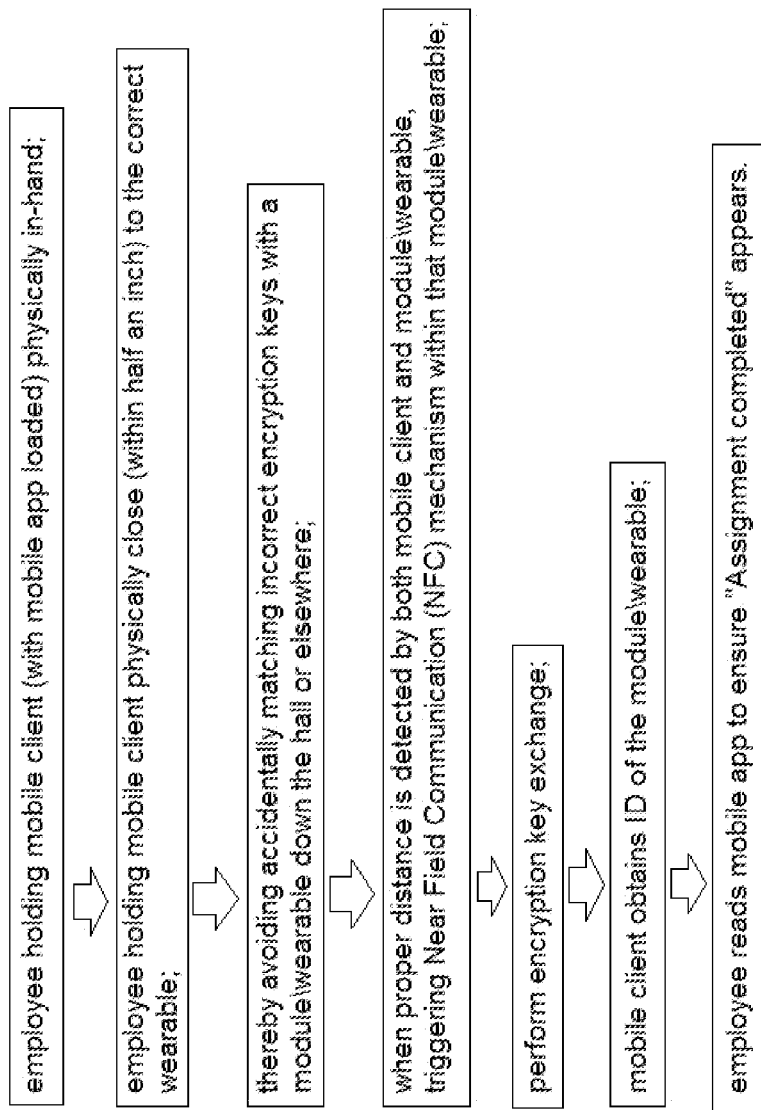
FIG. 4 shows a flowchart of an example Assignment process.

FIG. 4 shows an example non-limiting Assignment flowchart, a summary-only. Other steps may occur that are not shown in FIG. 4, and steps in FIG. 4 may occasionally be omitted. A typical health care employee, whether a nurse, attendant, relative, nurse's aide, or other caregiver, will have their mobile client 116 physically in their hand or on-belt, etc. During an Assignment process, the health care worker will hold the mobile client 116 close to the module\wearable 108 needing to be Assigned. They will then touch that module\wearable 108 with the mobile client 116 in order to use the Near Field Communication (NFC) mechanism within that module\wearable 108. Activating NFC works best being physically close to the NFC tag or to the LC antenna to read the data. So the health care worker will have to be in the proximity of that device to Assign that module\wearable 108 to a patient during the encryption key exchange, when the mobile application is grabbing (acquiring) an ID of the module\wearable 108.

During an Assignment process, the health care worker must be physically close to the correct wearable, and which avoids accidentally matching encryption keys with a device down the hall or somewhere else. Fortunately, avoid such a mis-match doesn't take much fool-proofing when NFC is employed. To take any Assignment action, the NFC mechanism requires the health care worker must have their mobile client 116 be physically close to that module\wearable 108 e.g. within half an inch.

Machine Learning

One advantage of the system 100 is the amount and volume of useful patient data that it generates. Another advantage of the system 100 should be (after an initial pain-period and learning-period) making the tasks of running and operating a residential facility or nursing home easier. But even further, the system 100 can also learn about the patients, anticipate problems before they happen, and make predictive intelligence about potential upcoming patient-problems, and perhaps either prevent such patient-problems or give better warnings.

Within this disclosure, the concept of machine learning is split into three phases.

The first phase is for the machine learning engine 136 (FIG. 1) to be able to figure out the thresholds basically automatically on its own, figure out what are the thresholds for each person, which means building that normal range for body temperature for this person, building that normal heart rate range for this person, because it's going to all differ per person, and then automatically adjust those things and be able to trigger the alerts when things are not normal. So being able to detect those anomaly conditions at the S as, as it gets more and more feedback from the nurse aides.

The second phase will be able to predict what's causing the problem. Let's say a patient has a flu or some kind of a respiratory illness, or a combination of things. To effectively detect such a condition and act upon it, the machine learning engine 136 may look at a pattern of heart rate differing by the temperature being different. There's all sorts of different patterns the system 100 might pick up on. In the second phase, predicting causes of Alerts may occur, and maybe even diagnosed to some extent. In the third phase, the system 100 will even suggest certain actions that nurses and caregivers could take.

Example of Second Phase of Machine Learning

The second phase will go into deeper machine learning including maybe trying to diagnose things, by e.g. adding more to the feedback mechanism including capturing what steps occurred to resolve an Alert. That creates more data for the machine learning engine 136 to digest. Once enough data is processed, once the machine learning engine 136 grinds sufficient material, the machine learning engine 136 would be able to start predicting options to try to solve a particular patient-health problem.

For example, assume a patient has low oxygen level. In the second phase, the system 100 might send out an Alert because there's a "low oxygen" alert from that patient. In the Alert Questionnaire (feedback mechanism contained within an app loaded within the mobile client 116), a Nurse or caregiver may note that in order to solve this, a health care worker bumped up the supplemental oxygen by one liter. The system 100 will also be informed that after that oxygen increase was completed, the patient's oxygen level normalized. The machine learning engine 136 might start recommending this in the future. That's just one example.

Alternatively, now assume a patient is running a fever and an alert is generated. Then, the nurse or caregiver responds within the Alert Questionnaire (with the app running on the mobile client 116) that the patient was given Tylenol, a specific dosage, and then the system will see the body temperature started to normalize. OK, that worked for that patient. However, for another patient, maybe Tylenol doesn't work, maybe something else works better to bring down the fever. The machine learning engine 136 would recognize this, and might make a variety of predictive recommendations, factoring in these differing conditions. The machine learning engine 136 thus isolate data-occurrences and alert-occurrences to a very fine granularity, that is, patient-by-patient. This avoids any temptation to over-extrapolate. Instead, the embodiments herein will just keep learning, and make the best possible use of the data gained.

Third Phase of Machine Learning

In that third phase, the machine learning engine 136 will suggest certain actions that nurses could take. That third phase requires a lot more testing and a different level of certification for the system 100. In the phase one, the system's primary job is going to be to monitor patients, not to treat and diagnose. But customers will quickly want to advance to the second and third phases.

In the third phase, the system dashboard 500 will potentially to allow employees to manage the system 100, manage facilities, run reports, and look at performance of various facilities. Someone could use the system dashboard 500 to run a report on the facility itself to find out an average number of alerts per day; OR how long are they staying open before being acknowledged? Also, how quickly they're getting resolved? All facilities strive to have such useful data metrics, but the system 100 has a strategic way of more effectively delivering these metrics, partly because of the contribution of the machine learning engine 136.

Next, the IAM (Identity Access Management) 152 provides a way to identify and authorize users of the system 100, of which there exist a wide variety of access levels. Meanwhile, OKTA is an example cloud provider that can support the IAM 152. Both are both HIPAA compliant, and thus suitable for authorize and authenticate users. Anytime the system dashboard 500, the facility dashboard 800, or a mobile client 116 talks to the cloud system 112, that access will get verified through the IAM 152 to make sure that they're a valid user.

Authenticate and Authorize

It is a goal of the embodiments herein to ensure that everyone accessing the system 100 have appropriate authorization. Accordingly, the IAM 152 first figures out whether someone is a valid user, and then figures out whether they have the proper access rights to access a specific resource in the system. The embodiments herein have usages that an admin user could do that an e.g. nurse cannot. If for some reason, a nurse tries to perform an action that they're not authorized, the IAM 152 will not allow them to do that. There may be one level below a nurse, e.g. nurse's Aide, perhaps also a second level below and maybe there's even a third level below, just the janitor-type or cleaning agency.

In an embodiment, there could be a person dedicated solely to making sure to Registering the modules\wearables 108. Setting up that encryption key mechanism described in e.g. FIGS. 2-3, that's the only thing they do. Dedicated. They are not Assigning the device to patients. The only thing they're doing is Registering it a brand-new module\wearable 108 with the system 100. Thus, the embodiments herein contemplate all different levels, an infinite number of different roles that that could happen in a residential facility or nursing home. Meanwhile, the job of the Okta and the IAM 152 is figuring out who is a valid user and whether they have the rights to access a specific resource of the system 100.

Zigbee v. Bluetooth, a Flexible Transition and Segue

One potential competitor to Bluetooth Low Energy (BTLE) is ZigBee. In the event it becomes necessary to get a divorce from Bluetooth and substitute ZigBee in the system 100, provisions presently exist. The system 100 is designed such that to segue away from BTLE, and put another mechanism in there, e.g. Zigbee, then the embodiments herein are only marginally impacted. For example, the cloud system 112 doesn't get impacted either way, and stays exactly the same.

Admittedly, during a BTLE-change will alter the module\wearable 108, e.g. new hardware to put in that can use ZigBee as a communication protocol. Basically putting in a different chip and a different antenna into the module\wearable 108, and then modifying the software in the smart hubs 104.

Moving to other aspects of a potential segue away from BTLE, as stated, the smart hub 104 doesn't have to be Raspberry Pi. In the event of a BTLE-divorce in favor of Zigbee, the smart hub 104 will be modified to be able to communicate over Zigbee. In such a BTLE-divorce, mainly two pieces get updated or upgraded: the module\wearable 108 and the smart hub 104.

Regarding the smart hub 104, Arduino is a microcontroller. Much smaller, less power, less expensive, than Raspberry Pi. Meanwhile, Raspberry Pi is a full-blown computer, facilitates everything one human does on a computer, e.g. watch movies, check email, or browse the Internet. Larger space, larger footprint, larger power supply thus larger power consumption. That is a type of "hardware overkill" for what the smart hub 104 really needs to achieve its purposes. A goal for the smart hub 104 is to employ a microcontroller designed to work on a low level, close to the hardware. Such a microcontroller may not have a lot of computing resources and may not need to. Within the embodiments herein, a smart hub 104 mainly monitors the communication and then passes the data along to the cloud system 112. This is true whether using Zigbee or BTLE.

When the embodiments herein move toward the Zigbee mechanisms, and go down to the Arduino route, they will then likely be implementing a "mesh" system. In some iterations, every smart hub 104 is connected to the cloud via e.g. Wi-Fi. Later, a mesh approach, has many smart hubs 104, but only one of these as a "master" smart hub that is connected to the cloud system 112. Let's say a given module\wearable 108 sends patient data over ZigBee. One of the smart hubs $104_1$ receives that data and passes it along to the nearest next smart hub $104_2$, that will pass it along to another smart hub $104_3$. There's going to be kind of one main central hub 104 that will be directly wired into the cloud 112. This central hub 104 will be "boss of the smart hubs". So as data bubbles up to that central smart hub 104, once that central smart hub 104 gets the data, it is directly wired into the cloud 112, thereby forming a mesh system where only one of the smart hubs 104 is connected to the cloud system 112.

Meanwhile, the other non-master (non-boss) smart hubs 104 act as little relays or beacons. They allow the data to hop along until it gets to the main central hub 104. That removes a problem of being tied to a facility's specific legacy infrastructure, such as not relying on a nursing home's (potentially crappy) Wi-Fi connectivity. Nursing homes are typically in the health care business, much more than in the IT business, although yes over time it's necessary to be in both, and the two can merge.

With a BTLE approach, it is necessary to do some things to make sure that communication is secure. With a Zigbee-based mesh approach, that becomes a lot simpler, e.g. an existing protocol that has the mechanism built in to exchange the encryption keys. This could also have the effect of removing the need to use the mobile client 116 to achieve initial Registration within the system 100.

Home Environment v. Residential Facility

The embodiments herein function both in a home environment and also in a residential facility. This means moving away from a residential facility (e.g. nursing home) and instead setting up ZigBee infrastructure in a consumer environment e.g. somebody's home. More friction and work is involved as Zigbee is less consumer-friendly that BTLE. Mobile phones usually do not come equipped with Zigbee. More learning curve and potential for error from a harried relative who must deal with a sick relative upstairs.

Instead, for now, the home-installation embodiment of the system 100 uses BTLE because everybody has a smartphone or mobile device that already has BTLE. That makes installation simpler. The embodiments herein strive to avoid requiring a PhD in Computer Science to install within the home environment. At least initially, having just one system 100 that's uniform across both the facility and the home makes it easier to roll out, as testing and debugging can be combined. Home users can learn Zigbee, but it's harder and less appealing.

The mesh approach is enhanced with ZigBee, as any dependency on having each of the smart hubs 104 be connected to the cloud system 112 will go away. Instead, only one smart hub 104 will be connected to the cloud system 112 by e.g. network cable and then the rest act as just little relays.

A goal of the embodiments is to not rely on whatever native Wi-Fi that a residential facility or nursing home have implemented. To first get into a new user's home, it may be suitable to perhaps borrow from their local native Wi-Fi for a little while, but transition away from that as soon as possible.

Thus, the embodiments herein are a combination of present and future, sometimes using with BTLE, even though Bluetooth doesn't yet support "mesh" as that term is sometimes understood. One embodiment has each one of the smart hubs 104 connected directly to the cloud system 112, and this is OK when it's inside a single-patient home, but not for a residential facility.

That's another factor to consider when installing a system 100 within a person's home. Most of the homes are not like mansions where they're so big to have a bunch of smart hubs 104. In a residential facility setting because of the large footprint, multiple smart hubs 104 are likely. However, in a single-patient home, mesh or no mesh, it doesn't really matter because most cases it's going to be just one smart hub 104 covering the whole home. This shows another nuance of the embodiments herein. A hybrid approach climbing BTLE and transition to full blown mesh ZigBee approach later, if necessary, and it may not be necessary.

It is possible to still have the module\wearables 108 communicate via Bluetooth to the smart hubs 104, but the smart hubs 104 will be able to communicate between each other via mesh (Zigbee). If that's solid, one can transition out of Bluetooth, start a divorce from BTLE if desired. At that point, such a transition is an easier "lift" to convince a customer, because there is no need modify any hardware within the module\wearable 108. All that is necessary is to modify the smart hub 104 to support ZigBee. In support of this, a Zigbee environment might have 200 or 300 module\wearables 108 versus 10 of the smart hubs 104, thus a much easier "lift" to sell and persuade a reluctant customer.

In the event of such a redesign of the wearable, either due to a BTLE-divorce or other reason: no need to get a new circuitry, new packaging. Whether Arduino or Raspberry Pi or other for the smart hub 104, it's usually going to be just a little USB dongle that plugs into the smart hub 104 that enables something to have ZigBee communication. Much easier "lift" and that could be something that would halfway transition, like "training wheels" before going to full blown ZigBee-only.

Conversely, another possible arrangement could take advantage of Bluetooth 5.0, especially considering that the module\wearables 108 have an upgraded Bluetooth chip that has better coverage than previous BTLE. This can result reducing the number of smart hubs 104 necessary to effectively implement the system 100. Even without Zigbee, e.g. staying with BTLE, this BTLE 5.0 advancement is still favorable, and still advantageous for end-users. While it's not Zigbee-mesh, it's still favorable.

The system 100 thus uses smart hubs 104 to be responsible for listening for data coming in, then taking that data and ensuring that it makes its way to the servers. Not granting access to anything. Instead, more like a "way station".

Mesh is another expression that is commonly misunderstood. What "mesh" means in the system 100: assume e.g. 10 smart hubs 104 in a facility. These smart hubs 104 will act as little relays between each other and bubble up the data to that single central smart hub, kind of the brain of the operations that will be directly plugged in into the cloud 112. The "mesh" principle is that one little one node passes data off to another node to another node until it gets to the end. That's the idea of mesh.

Conversely, the embodiments herein improved on the mesh technology where within a new mesh version, e.g. mesh 2.0, only one smart hub 104 needs to be connected to the cloud 112. And then the rest of the collection of smart hubs 104 in the mesh system 100 will be able to communicate with each other and ensure the data will eventually make it to the central (boss) smart hub 104.

The embodiments herein anticipate and solve another problem. Wi-Fi is not as stable as something that's plugged in via a physical wire cable. In some embodiments, of all the smart hubs 104, only the central hub 104 (the "boss" of all the smart hubs) has a direct wire connection to the Internet. The rest of the smart hubs 104 (non-boss) would only communicate with each other. That just means that only one smart hub 104 is depended on the facility infrastructure and the rest can communicate with each other.

Further, the system 100 can completely disconnect from a residential facility's specific Internet infrastructure where only the central (boss) smart hub 104 is connected to the cloud via a cellular signal. This way, the residential facility's specific Internet infrastructure can retain their own Wi-Fi. Thus, the embodiments herein are Wi-Fi agnostic.

Even in the facilities where the system 100 is directly plugged in to the facility Wi-Fi, crappy or not, the cell service will act as a backup. Let's say something happens and the Wi-Fi goes down. Want to have a backup plan. So if Wi-Fi is down, the system 100 starts utilizing its own cell-service to send data to the cloud 112. That also feeds nicely into kind of the evolution of the consumer product. Once we bring the cellular connectivity to these smart hubs 104, when entering the home-embodiment of the system 100, it's not necessary to connect their home (non-smart) hub to Wi-Fi.

Inside a typical home, they will have just one smart hub 104, so the footprint isn't that big. The embodiments herein can go full blown production, in the home, fully-enabled. From the beginning, the cloud system 112 is set up to accommodate multiple physical facilities at separate postal addresses and maybe even in separate cities. One way to "pilot test" is to just create five facilities. Each having only one patient for the beginning.

Begin System Dashboard 500

The system dashboard 500 embodiments described herein comprises a monitoring system, and an Alerting system, first and foremost. They are not meant to replace any kind of patient charts or facility medical diagnosis. Instead, the embodiments herein help enhance and facilitate effective and speedy diagnosis of problems within a residential facility or nursing home.

Alerts (Overview)

Figure 5:
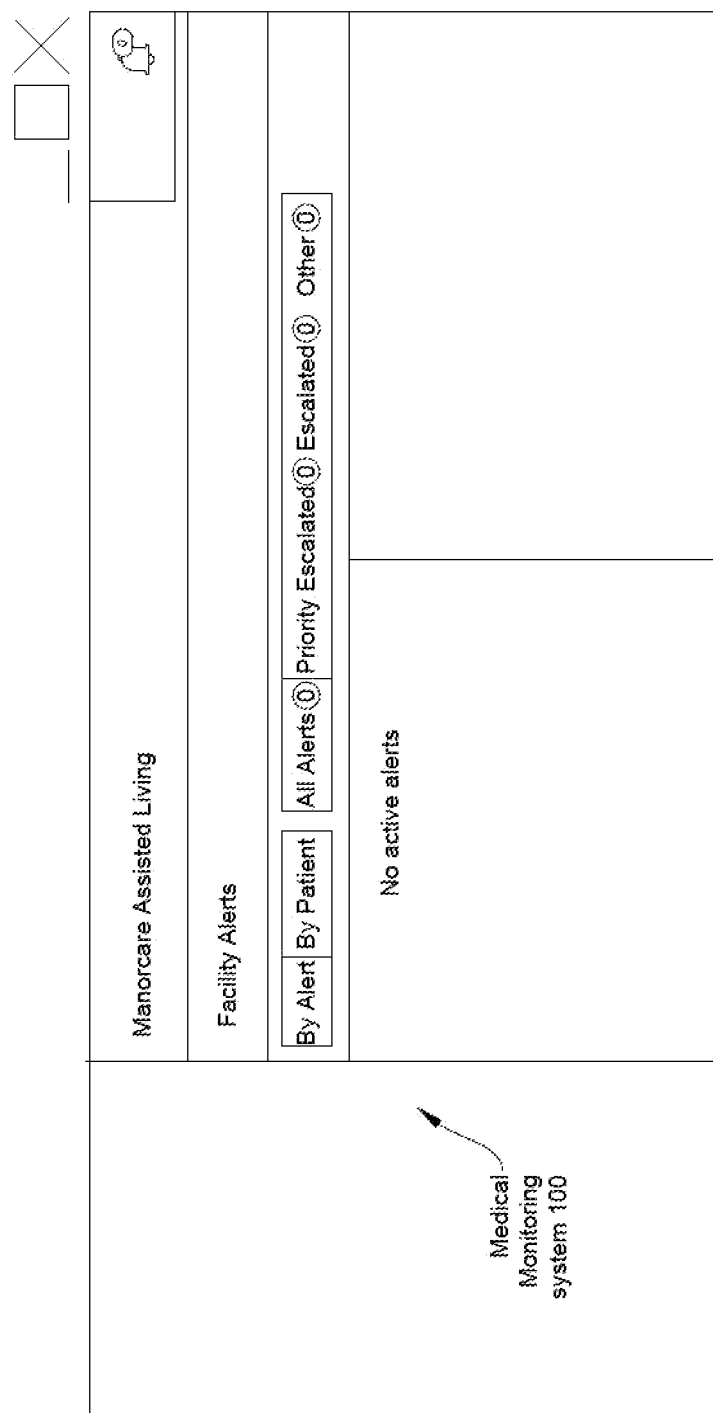
FIG. 5 shows an example Alerts page.

An example Alerts page is shown in FIG. 5, comprising active Alerts and Alert details. So, at the log in, users of the system dashboard 500 land at a list of all currently active Alerts, sorted by escalation level. For brevity, conciseness, and clarity, FIG. 5 is deliberately simplified showing an un-populated view without any Alerts, to de-clutter the image and focus on the other menu items. In the various Figures accompanying this disclosure, most Alerts will be the "other" level, which basically just means that they are not escalated in any fashion. If they were escalated, user could see the "priority escalated" bubble to the top, followed by "escalated", and then the "other". Additional categories could also be added.

Figure 10:
FIG. 10 also shows an Alert associated with patient Bobby Brown.

Similarly, Alerts can be grouped or sorted by patient. FIG. 7 shows Alerts sorted by patient, but then within the patient themselves, the Alerts can be further sorted by escalation level (e.g. FIG. 8). FIG. 9 shows that Ben Affleck here had a "priority escalated" Alert. Such Priority-Escalated Alerts would always appear right at the top. FIG. 10 also shows an Alert associated with patient Bobby Brown.

Figure 11:
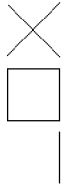
FIG. 11 shows examples of multiple active Alerts.

As shown in FIG. 11, patient Debbie Downer has three currently active Alerts, and FIGS. 6-7 show that Albert Finney has a couple. FIG. 6 shows selection of a hygiene Alert from Albert Finney selected. After selection, FIG. 7 then shows some details about that particular Alert, e.g. what module it came from (in this case, MOD-222-AF), a little bit more detail about this particular Alert. Then, the GUI in FIG. 7 displays some readouts of when the first Alert occurred, and how severe. The dashboard system 500 displays all of these factors, e.g. what value it was, the specific numeric thresholds that were breached, as well as other kinds of patient-data.

In another specific example GUI (FIG. 12), patient Albert Finney also has a position Alert, and users can see these Alerts are both still with an "open" status, so they don't have any results or resolution. Clicking on his position details will load the position one up here, so we can see more detail about it.

Varying the levels of the various Alerts facilitates workers paying attention to them appropriately. The embodiments herein also can tie in where an Alert changing levels escalates to a different worker-role, but right now it's mostly so health care workers can better filter out Alerts and quickly and instinctively see which Alerts require immediate action. Alerts that are Closed The system dashboard 500 will also display Alerts that were important at one time, but are now closed. Despite their being closed, users of the dashboard system 500 can still learn a lot from them. An example of patient Ben Affleck will demonstrate this in FIGS. 13-16, which has this current active Alert being "module disconnected". But patient Ben Affleck also has previous Alerts. For example, an Alert within FIG. 13 is closed and it's highlighted because it was inaccurate. If an Alert was responded to on the mobile app, there will likely be instances in which an investigation found an Alert to be inaccurate. Occasionally, Alerts that are later deemed inaccurate or invalid will occur. These invalid Alerts should not be considered an error or mistake, instead a learning opportunity.

This detailed view noted above will be on the same kind of section on Ben Affleck's patient page also. So that particular alert was set to "closed" as (partly) shown by the transition from FIG. 13 to FIG. 14. Next, it is important to note that Alerts can only be closed and reacted to by workers through the Alert Questionnaire on the mobile client 116. As such, closing of an Alert never occurs through the system dashboard 500 itself, instead the system dashboard 500 may reflect that an Alert is closed, in a variety of ways.

Figure 16:
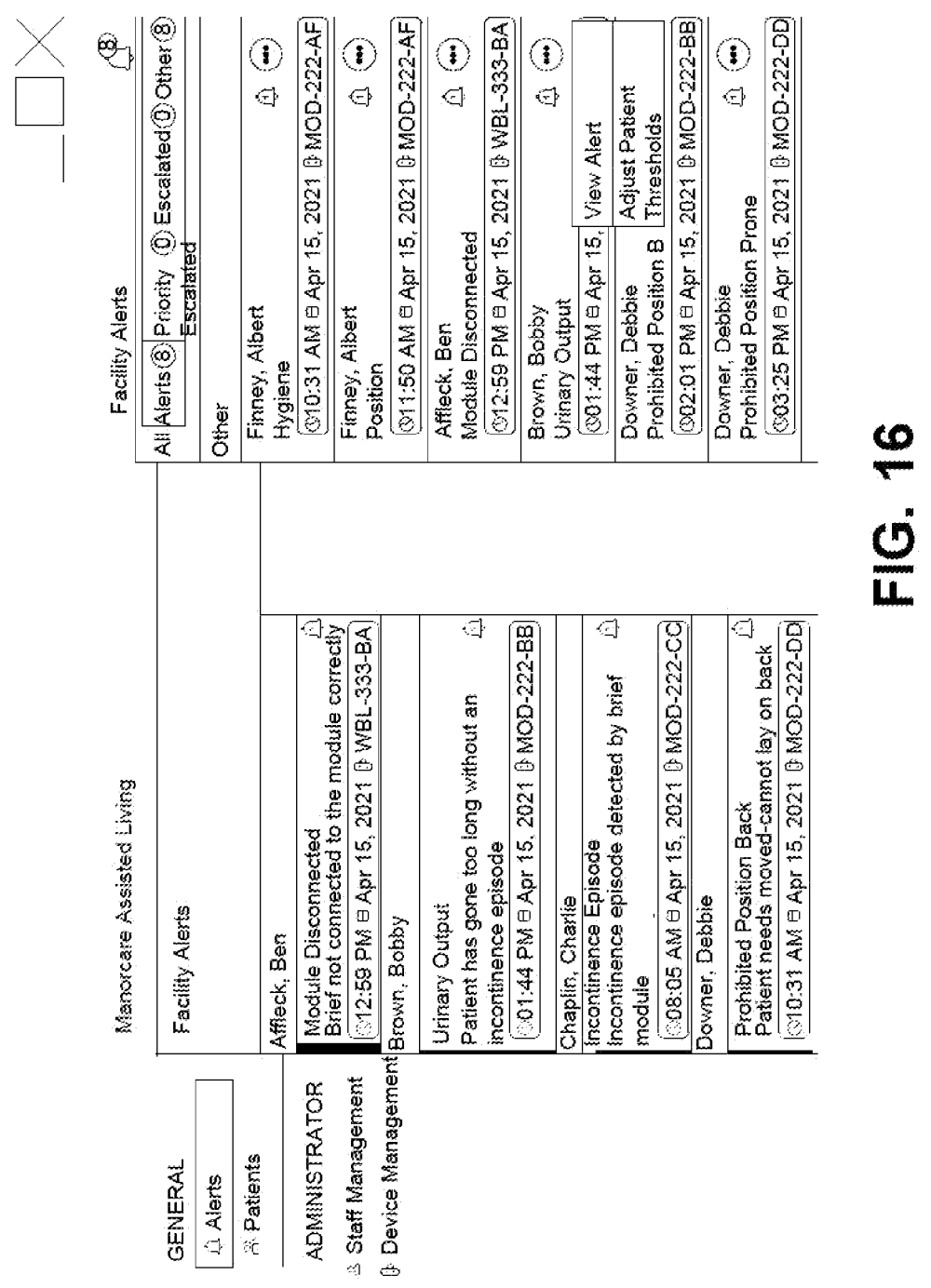

FIG. 15 is a GUI showing a user-selection of details from a column of Alerts related to patient Ben Affleck. FIG. 16 is a similar GUI, except that the column of Alerts related to patient Ben Affleck is removed. The point is to show some potential navigation paths within the various GUIs within the system dashboard 500, and that quick access to Alert data, through multiple GUI-paths, is facilitated within the system dashboard 500.

Active Alerts

Within the system dashboard 500, a list of all active Alerts is accessible from any page. The embodiments herein can sort Alerts into various categories, or to filter out different types of Alerts. FIGS. 6-9 all show an example of eight active Alerts. To best fully illustrate the embodiments, a different Alert is chosen that hasn't been described yet, specifically an Alert for Bobby Brown, as shown in FIG. 10.

Users can always navigate to any particular patient's Alert page. Setting aside Bobby Brown for a moment, it is possible to navigate from the GUI shown in FIG. 10 and pick e.g. Albert Finney's Alerts page. Doing that will navigate back to load Albert Finney's Alerts, as shown in FIG. 7.

Example alert cards are shown in FIG. 7 and also in FIG. 12. Navigating to a positional Alert from Albert Finney shows a time\date when the happened, and which particular device triggered the Alert.

Chains of Alerts

Thus far, all data-fields corresponded with just a first Alert. That's what the number one means with the (example) bell icon 704 shown in FIG. 7 (and numerous others). If there were other data-items in a particular chain of Alerts, the system dashboard 500 would show them as well.

Within this disclosure, the expression "chain" of Alerts means a specific Alert has triggered more than once. That is, the repeated Alert does not reflect some new issue, but is merely repeating that an earlier issue has not yet been addressed. From FIG. 17 it is apparent that patient Andy Capp has a couple of heart rate Alerts. Users can see the first Alert was "escalated" because of the particular measurement automatically came in as escalated rather than something else that would be kind of a standard Alert. There exist particular rules around which Alerts get escalated and how that happens.

Assume a particular Alert was escalated, and thus now a user has navigated to a second Alert. The bell icon 1704 in FIG. 17 indicates this by showing a two (2), indicating something is a second Alert. Specifically, this second alert also shows "priority escalated". As such, navigating the system dashboard 500 to filter out anything but priority (e.g. selecting the highlighting 1708), users only see this one Alert. The same filtering can be done on "escalated" status.

Figure 17:
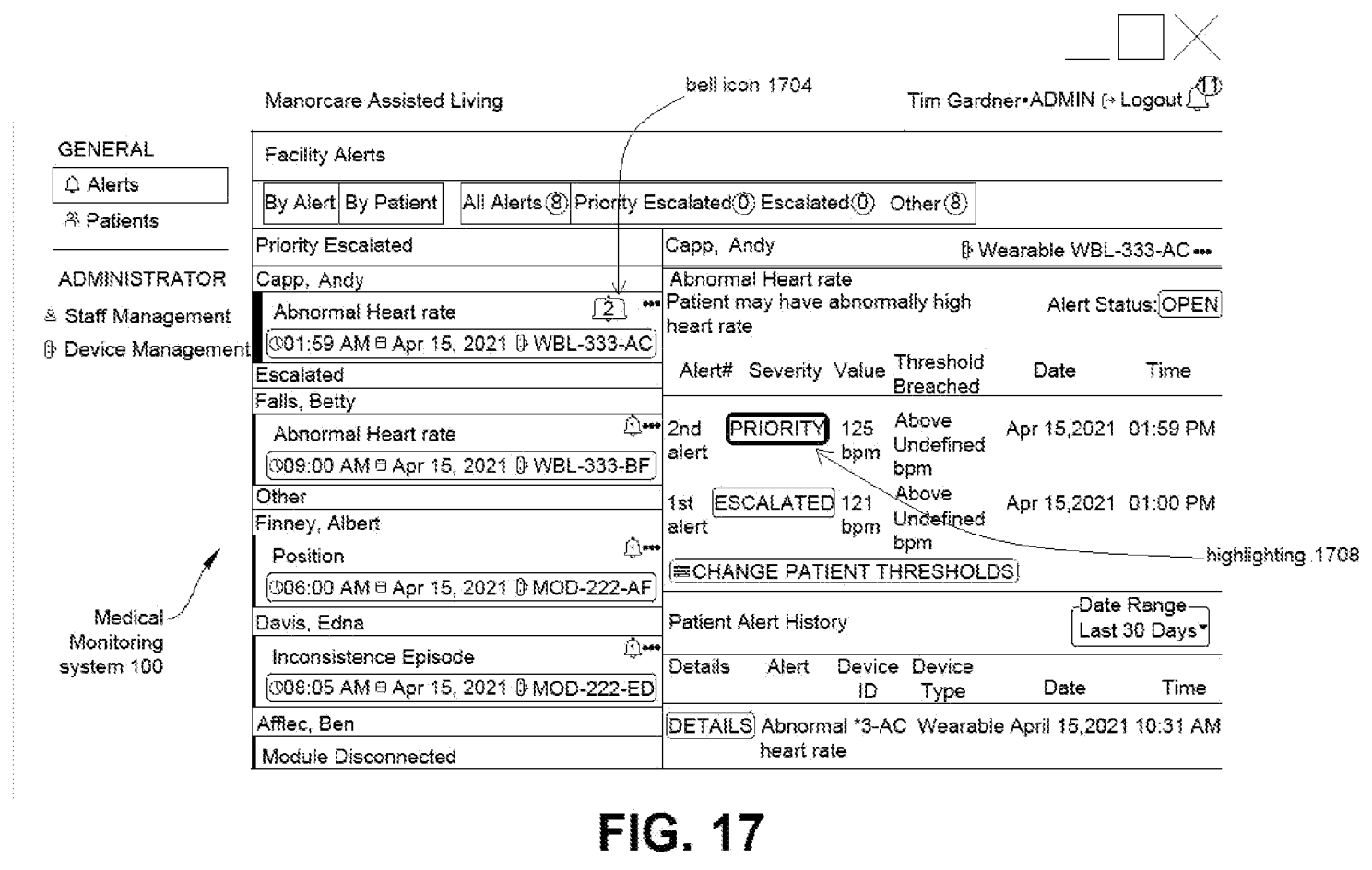

The results are a matter of what has happened with that chain of Alerts. One can see this from viewing FIG. 17, in which a key Alert is still in an "open" status. This particular abnormal heart rate Alert suggests (but does not guarantee) that Betty Falls has an abnormal heart rate, but also had an incontinence episode, as both of those are still "open". Meanwhile, Ben Affleck had an Alert that was closed. Again, the various Alert histories shown in FIG. 17 are not included herein to convey any details about a particular Alert. Instead, FIG. 17 and other sections herein are meant to convey a result, outcome, and visual flow of a chain of alerts.

Navigation Principles and Usability

The overall layout of the various GUIs within the system 100 are meant to be similar across all of these views. Main navigation features are always on the very left of a viewer's page, list of whatever is needed to work with in the left of middle column, and details on the right. The system 100 strives to keep it similar so that workers and other people would quickly understand the visual flows and transitions, no matter what specific screen or GUI a user is currently navigating.

Moving back to usability aspects of the system 100 and of the various GUIs within the system dashboard 500, the various Alerts are color coded, which is important for quick recognition. Knowing that health workers have many other tasks and obligations, including the health and welfare of people who may be helpless or incapacitated, the embodiments herein strive to avoid being an IQ test for healthcare workers, or require a PhD in computer science to operate. Instead, the system 100 strives to eliminate visual clutter and un-necessary complexity, and focus mainly on helping the patient, helping the facility, helping their employer, and helping to make their own jobs easier. Thus, color-coding is used to briefly and instantly convey severity of Alerts, specifically Red, Yellow, and Green tone. Green connotes a standard Alert, a regular garden-variety Alert. Yellow is more important. Red is the most important.

This color-coding is carried throughout all of the clients and all of the dashboards and views. The intent is to be intuitive, not require complex mental decoding or training.

Facility Dashboard 800

The system dashboard 500 does not extend outside the walls of a particular facility. So, it would be accessible and useful only by whoever is physically within that facility. In certain cases, the system dashboard 500 will notify nurses or members that are part of a specific facility, but it doesn't extend past that.

Meanwhile, the facility dashboard 800 coordinates multiple facilities. In the home-use embodiment, the facility dashboard 800 is not needed and will likely be disabled, or will not contain anything.

Using Metrics and Measurements to Customize Alerts

The embodiments herein incorporate results of a module\wearable 108 taking patient measurements. If those measurements exceed the bounds of these thresholds, then thresholds are breached, and customized Alerts can be generated. Looking at measurements to have exceeded thresholds. Particular Alerts are even more important, they escalate the severity level of the Alert. This principle is best demonstrated at least within FIG. 17. This is because 121 BPM for e.g. patient X, for example, could be a severe problem. However, for another particular patient Y, even 125 BPM may not be anywhere near the same threat-level.

Thus, as part of on-going process improvement, the embodiments herein incorporate feedback from users and will adjust accordingly. The embodiments herein strive to be on the side of useful, not annoying, and enhancing their workflow but not creating new workflow. Applicant also strives to make the dashboard GUIs readable and salient. That is, within the overall system 100, there exists some complicated medical data to look at and display, often high volumes of data. Accordingly, the embodiments herein strive to make that data as readable as easily as possible for anybody, including facility-workers having minimal reading-comprehension levels. The embodiments herein strive to make sure that the facility-workers can use and understand the system dashboard 500 and facility dashboard 800.

Using the GUI within FIG. 22 as an example, it is possible to configure an abnormal heart rate Alert according to one specific patient: a heart rate below 50 generates an Alert; a heart rate above 150 generates an Alert. Thus, for that one patient, a heart rate between 51 and 149 would not generate an Alert. Those numbers might be that specific facility's default numbers, but this particular patient has "override" so that if their measurements are outside of 60-130, that's when they will trigger an Alerted. This feature is demonstrated at least within FIG. 22.

Using Images of Patients

Next, knowing that workers in a residential facility or nursing home may be 1) tired and 2) have limited professionalism and ability to correlate names with specific patients, it may be possible to modify the mobile app running on the mobile device (AKA mobile pager) to add photos of the residents, or of the patients, to their data-profiles. However, to do would require building out some cloud storage, choosing an image-format which loads and stores quickly, and other factors. Next, a specific location to store those images would be needed. These files need to live somewhere, and uploading them and all the file-management details is considerable. But this feature properly implemented could make the health care worker's tasks easier, and reduce (potentially) obvious errors.

Clicking the button in FIG. 18 will take users to a particular patient in the patient view, and will enable modifying that patient's thresholds for a particular set of these rules. So users with the right access privileges can set rules for specific patients. To demonstrate this feature, the GUI shown in FIG. 7 gets Albert Finney's Alerts is referred to.

Figure 20:
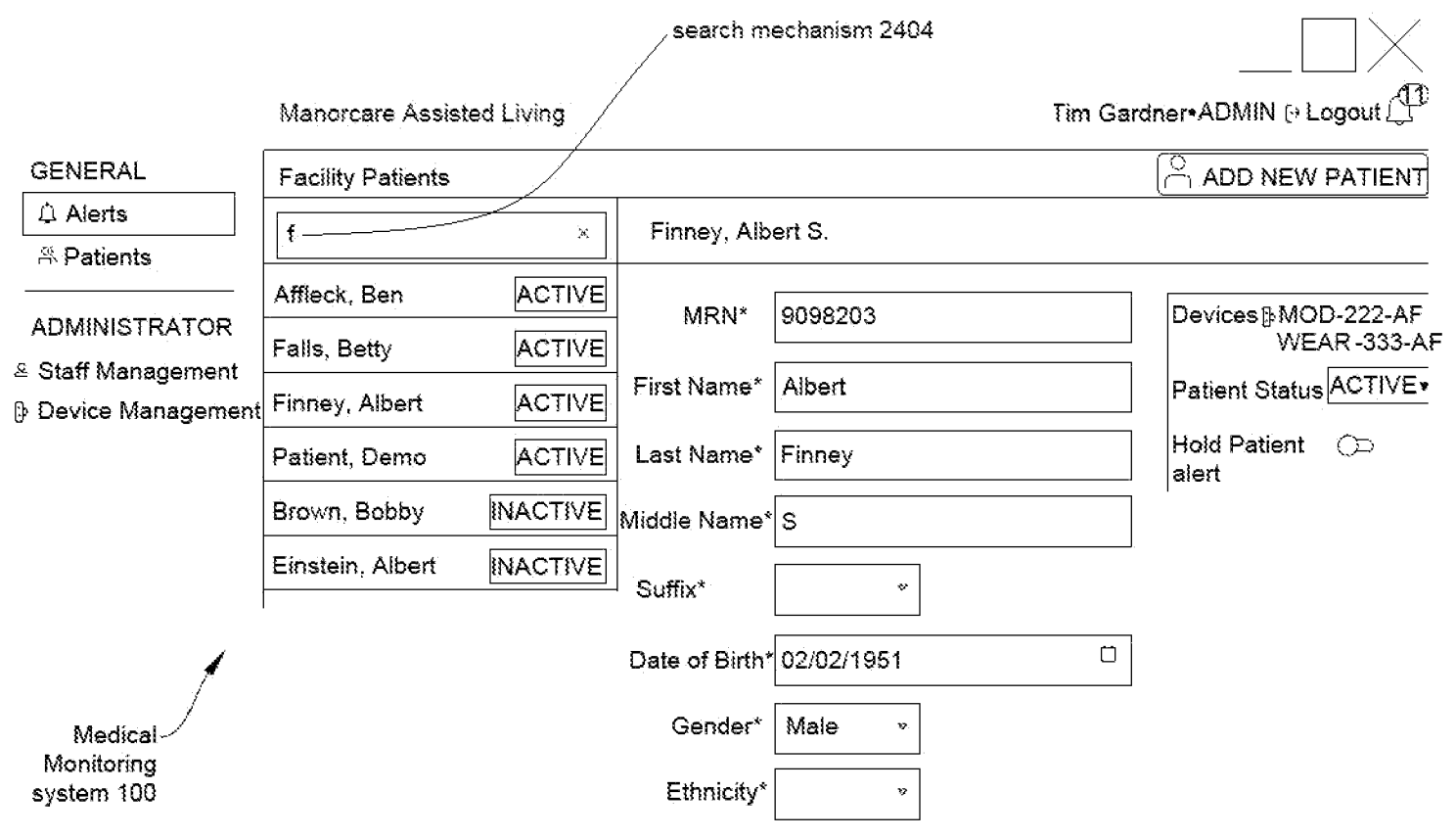

One can also the system dashboard 500 interface to search for specific patients. Doing an example search on F as shown in FIG. 20, searching for an F at all, there's people that haven't any F in their name showing. We will assume that Mr. Bobby Brown was probably found by error, or has some other F in his profile. We search on Ben, which has an F, should find Ben Affleck and it did. The use of 'F' should have found Albert Finney, but something went wrong.

The GUI shown in FIG. 19 is included to convey an example column of patient data. The scope of this particular column in FIG. 19 is to show specific types of Alerts. The reason temperature Alerts exist is there could be measurements for temperature from both a wearable $108_w$ and also a module $108_m$. The various devices 108 that a patient has e.g. Albert Finney are shown at least within FIG. 20.

Thus, within the system 100 and the system dashboard 500, the various module/wearable devices 108 that are assigned to a patient will always be listed out for review. This is useful for acting as a "check" and verification of the Registration and Assignment processes referred to at least within FIGS. 2, 3, and 4. From FIG. 20 it is apparent that Albert Finney has two devices 108, module MOD-222-AF and wearable WEAR-333-AF.

Figure 21:
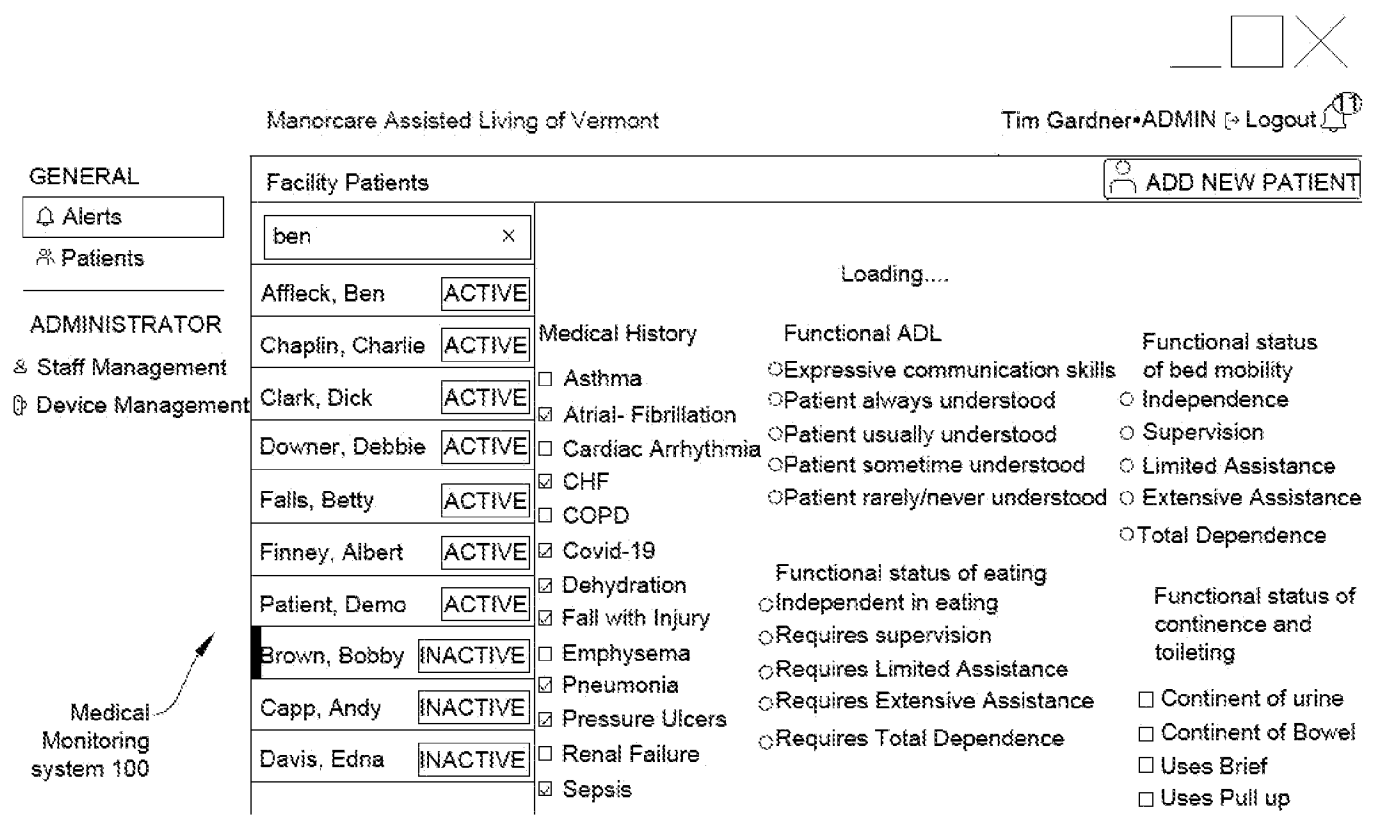
Figure 23:
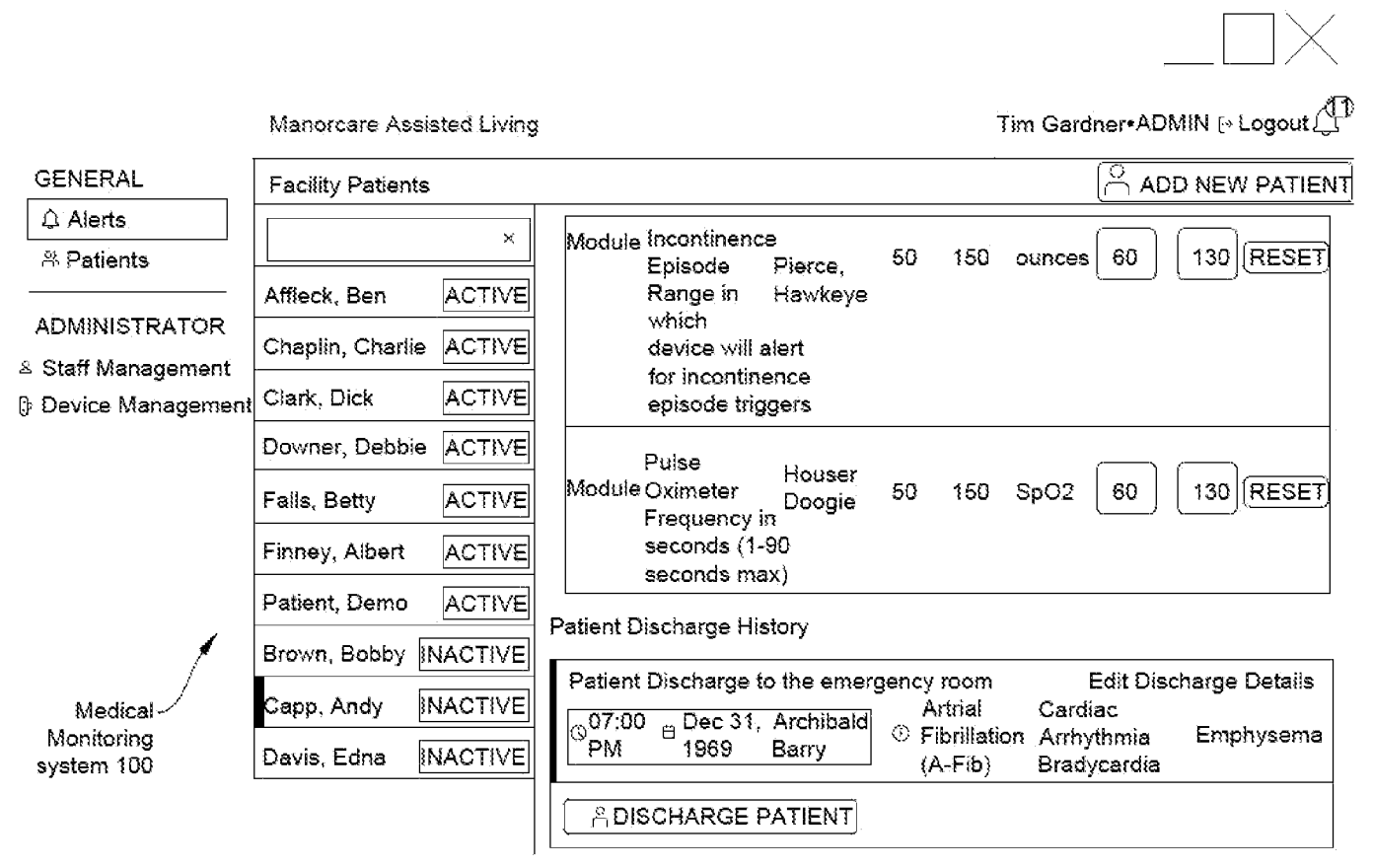

FIGS. 21-23 illustrate an ability to search or rather filter on "active" or "inactive" for patients. If a patient is active or inactive, user will be able to sort on that, like sorting on Alerts where users can pick a button for showing only "active" or only "inactive" Alerts.

The embodiments herein strive to accommodate the needs of a nursing home and those patients. Another feature is an ability to "hold" patient Alerts so they can remain active in the system 100, as shown in FIG. 20, but may be held in abeyance. Suppose a patient leaves the facility physically, the system 100 won't be chiming off a whole bunch of pointless Alerts, thus negating a semi-Spam effect. When that patient comes back, their Alerts will start triggering again.

Meanwhile, when someone is "inactive", that is more of a permanent situation. Either they have left the facility permanently, or they have been released, they're going home, they're going somewhere else, perhaps dialysis, or they are dead. Thus, the "active" or "inactive" is more of a permanence indicator, where "hold" on Alerts is more temporary. If someone is inactive, one can reactivate them. FIG. 23 shows that patient Andy Capp has been discharged to an emergency room.

Within the embodiments herein, no data is deleted, but may be put into a "disabled" state. Functionally, what that means is that the data is all still there, all the measurements, all of their alerts, all that data still remains present. The data is not removed, they just will no longer trigger any Alerts. This can be helpful for patients who later try to say they were mis-treated during their stay.

Factors Related to Size of Facility; Home V. Residential

In a home-version, in the case of taking care of just be one person, a "facility-name" field might contain something meaningless or unimportant, or perhaps may not be filled in at all. However, the embodiments herein contemplate working across multiple facilities. If just taking care of one's parents, then there may be just one or two patients, so that a facility-name might not be important. In such a situation, the facility dashboard 800 (FIG. 1) could be removed or disabled.

Next is the concept of the system dashboard encompassing multiple facilities belonging to multiple facilities. Users would have a similar group of list items in the navigation section. Instead of "general" or "administrator" group, the system 100 would display something like "environment", and under that, users could see "facilities", and then display all the facilities visible across an entire system 100.

Family members (not healthcare workers and professionals) using the system 100 will have different needs, and potentially more obstacles, than residential facilities or nursing homes. So there's possibility that the GUIs within the embodiments herein will diverge. Initially, the GUIs for both home-care and residential facilities are very similar, but there's nothing in the system 100 requiring the same GUI for both. Family members may require other features, or maybe convey information in a different way, the system 100 has the adjustability and flexibility to accommodate that.

FIG. 21 shows a typical patient's details, plenty of detailed information. This may include but is not limited to problems they may have experienced in the past, their statuses, perhaps what kind of oversight they might need within a residential facility or at home. This allows sorting for patients that have these particular disabilities, have specific Alerts, etc. This is the sort of stuff that feeds into machine learning engine 136. This ends the section on sizes and numbers of facilities.

Position Data

Another feature of the system 100 is "prohibited positions". GUIs can have lists and select boxes saying e.g. patient can't be placed on their left, right, back, front, or they can't stand for long periods of time. If they're on a certain side for too long, it is helpful to trigger an Alert. Numerous examples of positional Alerts occur in this disclosure, including at least FIGS. 6, 7, 9, and 10, including but not limited to patient Albert Finney.

Regarding patient Alerts, an embodiment of a module 108 used within the system 100 has an enhanced chip set, with a gyroscope and accelerometer. This results in higher resolution and accuracy on knowing a patient's body-position and/or body-orientation. It will also result in reducing false Alerts that are not needed, and clutter up the system 100. If the system 100 detects positional examples of reduced less accuracy or off-calibration, there are steps available to improve accuracy. Just one step of numerous examples is correlating patient-position data, especially aberrant or anomalous position data, with data of that same patient obtained from a different wearable 108 e.g. wrist or earlobe. The goal is to have ability to detect positions and quickly identify positional problems accurately.

Module v. Wrist-Wearable v. Other Devices

Depending on the diagnosis of the different problems a patient is suffering from, it may be required that a patient has both a module 108 plus a separate wearable 108 e.g. wrist-wearable, versus just one module/wearable 108. Further, the system 100 accommodates multiple module/wearables 108, where not all of these devices need to be on-body. Potentially there could be devices in the room monitoring air/lighting environment, air quality, the amount of UV exposure, amount of ambient noise (e.g. jackhammers or construction), is a patient getting enough sunlight? or light as a whole? Further, as mentioned earlier, the wearables 108 could also be worn on the toe, on the earlobe, or other body locations.

Thus, multiple module\wearables 108 can be assigned to a person. For example, an embodiment exists in which a non-intrusive blood glucose monitor is attached to an earlobe. Further, an embodiment exists in which a non-intrusive dehydration monitor is attached somewhere on a patient's skin.

Discharge of Patients (why Confusing)

What follows is an example of the documenting, whether suspected or confirmed, of the potential reasons why a patient was discharged. Let's suppose that Andy Capp has been discharged from a residential facility or nursing home to an emergency room.

In trying to document and affirm discharge a patient, users of the system dashboard 500 can select different discharge-locations. For some discharge-categories, no sub-choice GUIs come up, no sub-choices for e.g. "destination". However, for other discharge-categories, e.g. emergency room or hospital, then the user is given further options to pick from. However, the specific users operating the GUIs within the system dashboard 500 don't have to pick anything, are not software-forced to select anything, as they may not know. In the case that somebody is discharged to the ER, all parties want the system 100 to know that fact, although they may not know why a discharge was necessary.

Let's say a nurse assistant, nurse aid, or whatever other level or employee-classification or position, is just doing data-entry or data-cleanup. Facility admins may be the only people that are able to authorize a discharge anyway, but setting aside authorizing a discharge, instead consider documenting a discharge. These are two different things, with two different levels of information-accuracy.

A clerical person can at least enter that a discharge occurred, but they will probably not know specifically why, but they may guess "well, yeah it was COVID 19". They might then surmise "that's why I think this discharge happened, and so I'll submit it until better information arises". If someone else later had better information, they could edit this field. For example, a user of the system dashboard 500 might say "okay, actually it wasn't COVID-19, it was asthma" or something like that. So other dashboard-users can modify data after the fact, but the system 100 will know where and when the data was modified, thus preserving data-integrity.

Nobody wants false or inaccurate data, but there may be instances within the system 100 where even some potentially speculative data is still better than nothing. To bolster data-accuracy, every action that the user takes to modify data, modify patients, all of that is data-logged and available for later review. For example, FIG. 23 shows that a facility-worker Barry Archibald modified certain data, but even if another user were to later modify this data, the system 100 would also still have the record of Barry Archibald making this discharge initially. This achieves a type of "blockchain" effect. In this way, the system 100 will include numerous checks and balances for ensuring data-accuracy, including allowing for updating data as more information becomes available, but also allowing health care workers to have flexibility to enter what (limited) data they may have at a given time.

Within the embodiments herein, users of the system dashboard 500 can also navigate to a "staff management" GUI. This is very similar to patient management, but is instead more oriented toward staff. The facility dashboard 500 includes an active\inactive filter, somewhat like for the Alerts, and for the patients. This feature can be adapted to display staff who are deactivated or have other statuses.

Regarding the staff management GUI-set, the system 100 facilitates facility administrators being the only ones to have a certain views. Got multi levels of users and these levels are all tied to their job-title, which can include RN's, nurse's Aides, LPN, and numerous others which will change over time. Admins, Aides, and Don's, can all be set as facility administrators, IOW they can have the "keys to the castle". An LPN or an RN, might have access to the system dashboard 500 where they can see the Alerts and patient-views, but when they are on the patient's page, they can't make any changes. They only view the data, but they can't edit any of it. Read-only.

Similarly, other job-classifications such as nurse's Aide or other admins also cannot modify this data. Some labor-classifications may not have access to the system dashboard 500 at all. Certain levels of staff can only use the app on the mobile client 116, but not the system dashboard 500. Even the mobile app within the mobile client 116 exists mainly for purpose of responding to Alerts. As such, for certain levels of staff, that's really the full extent of their data-exposure within the system 100. They get Alerts and they can say "yep, I've acknowledged that Alert" and maybe make some other selections, document some status issues. That may be all some labor classifications (levels of staff) can do, where they don't have any access to the system dashboard 500. These access-rights are managed partly by the IAM 152.

Specific Hardware

A user could probably use the system dashboard 500 on a tablet, perhaps, but with difficulty. An intended environment for the dashboard described herein might be a laptop with a 13-inch screen. Anything much smaller than that starts to get pretty cramped and congested. A tablet in this kind of a horizontal layout of the system dashboard 500 might\could work, be viewable, but with plenty of frustration. The system dashboard 500 is not intended to be mobile-device friendly or tablet-friendly.

Disclaimer

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations, or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A method of configuring a medical monitoring system, comprising:
    positioning one or more wearable devices onto one or more patients, each patient wearing at least one of the one or more wearable devices;

the one or more wearable devices wirelessly communicating medical data to one or more smart hubs;
configuring one or more mobile clients to receive medical alerts regarding a particular patient and to respond to those alerts;
equipping each of one or more health care workers with one of the one or more mobile clients thereby facilitating the one or more health care workers having the ability to respond to the medical alerts;
the one or more wearables arriving to a facility in an un-registered state;
as part of a facility registration process, setting a first of the one or more wearables into a special pairing mode;
once the special pairing mode happens, an app running on the mobile client setting up a secure connection, where the app will receive a passcode generated by the first of the one or more wearables, as well as generate its own special encryption key;
comparing the special encryption key and the passcode;
if they match, that establishes that secure communication between the first of the one or more wearables and the app on the mobile client;
if they don't match, something went wrong in the registration process and the app will post an error-GUI;
the medical monitoring system facilitating both a special pairing mode and a normal pairing mode between one of the one or more wearables and one or more of the one or more smart hubs;
the special pairing mode occurring during the facility registration process wherein each time one of the one or more wearables is registered, generating a new special encryption key;
the normal pairing mode occurring during normal everyday use of the one or more wearables and the one or more smart hubs;
during the normal pairing mode, the app on the mobile client inquiring to the cloud system for the cloud system to generate the normal encryption key, after which the cloud system will send the normal encryption key to the mobile client, and then the mobile client will send the normal encryption key to the wearable for use in the normal pairing mode and a normal broadcast mode;
while generating the normal encryption key, the cloud system assigning that key to an ID of that wearable.

2. The method of claim 1, further comprising:
encrypting all communications either to or from the one or more smart hubs, such that hacking or invading or ransom-izing a smart hub yields only encrypted data that would still need to be unencrypted to be usable;
an IOT hub component within the cloud system looking up the normal encryption key and decrypting encrypted data sent by the smart hub; and
storing that decrypted data within an event hub for long-term storage and blob storage.

3. The method of claim 2, further comprising:
all of the one or more smart hubs directly communicating with the cloud system.

4. The method of claim 2, further comprising:
exactly one of the one or more smart hubs directly communicating with the cloud system and acting as a boss smart hub;
all other smart hubs all acting as relays that pass data to the boss smart hub.

5. The method of claim 1, further comprising:
the app generating the special encryption key; and
the cloud system generating the normal encryption key.

6. The method of claim 5, further comprising:
the medical monitoring system achieving registration of the one or more wearables whether the one or more wearables is on or off a patient's body.

7. The method of claim 5, further comprising:
configuring exactly one special encryption key for exactly one of the one or more wearables at a time;
facilitating any of the one or more wearables to be re-usable and re-registrable;
each time a one of the one or more wearables gets re-registered, discarding the old special encryption key and the cloud system creating a new special encryption key.

8. The method of claim 5, further comprising:
the app running on the mobile client acting as a status indicator and problem notifier for one of the one or more wearables.

9. The method of claim 8, further comprising:
a health care worker possessing one of the one or more mobile clients and using that mobile client for assigning a specific wearable to be worn by a specific patient;
the health care worker holding the mobile client physically close to a specific wearable thereby avoiding any accidental match with a separate and non-intended wearable;
assessing and making a determination about a distance between the mobile client and the wearable;
when the distance is deemed sufficient, triggering a near field communication mechanism within the specific wearable;
when the distance is deemed sufficient, intentionally avoiding triggering a near field communication mechanism within any other wearable other than the specific wearable;
performing an encryption key exchange between the mobile client and the specific wearable;
the mobile client obtaining the ID of the wearable; and
the health care worker reading the app within the mobile client to ensure an "assignment completed" message appears.

10. The method of claim 9, further comprising:
the encryption key that is part of the encryption key exchange comprising the normal encryption key.

11. The method of claim 9, further comprising:
the medical monitoring system requiring that a successful registration occur prior to any attempt at assignment beginning.

12. The method of claim 11, further comprising:
the smart hub conveying only encrypted data, where the special encryption key and normal encryption key are inaccessible from the smart hub; and
insulating the smart hub from either storing or conveying any non-encrypted or patient-sensitive medical data.

13. The method of claim 12, further comprising:
in the event of a data hack of any of the one or more smart hubs, preventing the data hack from yielding any data about any patient.

14. The method of claim 11, further comprising:
arranging that the one or more smart hubs be incapable of decrypting any data passed therethrough;
the one or more smart hubs forwarding all data through an Internet connection to the cloud system and then to an IOT hub;
the IOT hub and cloud system looking up the normal encryption key;

decrypting the data therein; and putting that raw data into the event hub, at which point the raw data will be stored for long-term use within the blob storage.

15. The method of claim 1, further comprising:

at the one or more mobile clients, configuring an alerts questionnaire so that at log in, workers first landing at a list of all currently active alerts;

the alerts questionnaire sorting the alerts by escalation levels comprising priority escalated, escalated, and other; and facilitating that additional escalation levels can be added within the alerts questionnaire.

16. The method of claim 15, further comprising:

facilitating sorting of alerts by patient;

within the patient alerts, sorting the alerts by escalation level, thereby facilitating workers paying attention appropriately; and arranging that an alert changing escalation level may result in a different worker-role responding to that alert.

17. The method of claim 15, further comprising:

arranging that alerts are only closed and reacted to by workers through the alert questionnaire on the mobile client and that closing of an alert never occurs through a system dashboard.

18. The method of claim 15, further comprising:

configuring the alert questionnaire to manage alerts that have been triggered more than once in a chain context such that a chain alert does not reflect some new issue, but is merely repeating that an earlier issue has not yet been addressed; and a GUI showing how often a chain alert has been repeated.

19. The method of claim 14, further comprising:

arranging that a patient discharge may be authorized and documented, wherein the discharge authorization and discharge documentation may be separate tasks having different levels of information accuracy and performed by different workers;

arranging that other workers can modify discharge documentation data after the fact, but the medical monitoring system will record where and when the discharge documentation data was modified.

* * * * *